United States Patent
Fukagai et al.

(10) Patent No.: US 7,596,993 B2
(45) Date of Patent: Oct. 6, 2009

(54) DIAGNOSTIC METHOD AND APPARATUS FOR GAS SENSOR

(75) Inventors: Reina Fukagai, Aichi (JP); Norikazu Ieda, Ichinomiya (JP); Masahiro Tanaka, Kasugai (JP); Hiroshi Inagaki, Komaki (JP); Masaki Hirata, Hamamatsu (JP); Takahiro Suzuki, Hamamatsu (JP)

(73) Assignees: NGK Spark Plug Co., Ltd., Nagoya-shi (JP); Suzuki Motor Corporation, Hamamatsu-shi (JP)

( * ) Notice: Subject to any disclaimer, the term of this patent is extended or adjusted under 35 U.S.C. 154(b) by 0 days.

(21) Appl. No.: 12/283,440

(22) Filed: Sep. 12, 2008

(65) Prior Publication Data

US 2009/0084172 A1 Apr. 2, 2009

(30) Foreign Application Priority Data

Oct. 1, 2007 (JP) ............................... 2007-257807

(51) Int. Cl.
*G01M 15/04* (2006.01)

(52) U.S. Cl. .................................... 73/114.72; 73/23.31

(58) Field of Classification Search ........................ None
See application file for complete search history.

(56) References Cited

U.S. PATENT DOCUMENTS

| | | | | |
|---|---|---|---|---|
| 4,938,194 A | * | 7/1990 | Kato et al. | 123/688 |
| 5,052,361 A | | 10/1991 | Ono et al. | |
| 5,179,929 A | * | 1/1993 | Miyashita et al. | 123/688 |
| 5,416,710 A | * | 5/1995 | Kuroda et al. | 701/104 |
| 6,360,583 B1 | * | 3/2002 | Soltis et al. | 73/23.31 |
| 7,142,976 B2 | * | 11/2006 | Inoue et al. | 701/114 |
| 2004/0238378 A1 | * | 12/2004 | Kumazawa et al. | 205/781 |
| 2005/0288847 A1 | * | 12/2005 | Inoue et al. | 701/114 |
| 2006/0157348 A1 | * | 7/2006 | Inoue et al. | 204/401 |
| 2007/0272551 A1 | * | 11/2007 | Inagaki et al. | 204/406 |
| 2007/0273540 A1 | * | 11/2007 | Inoue et al. | 340/632 |
| 2008/0060939 A1 | * | 3/2008 | Inoue et al. | 204/401 |
| 2008/0060941 A1 | * | 3/2008 | Ieda et al. | 204/431 |
| 2008/0196489 A1 | * | 8/2008 | Fukagai et al. | 73/114.72 |
| 2008/0196490 A1 | | 8/2008 | Fukagai et al. | |
| 2008/0196702 A1 | * | 8/2008 | Fukagai et al. | 123/688 |
| 2009/0095052 A1 | * | 4/2009 | Inoue et al. | 73/23.32 |

FOREIGN PATENT DOCUMENTS

JP          03-202767          9/1991

* cited by examiner

*Primary Examiner*—Andre J Allen
*Assistant Examiner*—Freddie Kirkland, III
(74) *Attorney, Agent, or Firm*—Flynn, Thiel, Boutell & Tanis, P.C.

(57) ABSTRACT

A gas sensor diagnostic method includes the steps of counting the reversal number of times that a target air-fuel ratio for an air-fuel mixture to be supplied to an internal combustion engine reverses from a rich side to a lean side or from the lean side to the rich side through a specific air-fuel ratio defined as a boundary of the rich and lean sides; obtaining a detection signal of gas sensor at constant time intervals during a diagnosis period between a timing when the count for the reversal number is started and a timing when the reversal number reaches a predetermined number; calculating a first moderated signal by applying a first moderation calculation to the detection signal, and a second moderated signal by applying a second moderation calculation to the detection signal; calculating a deviation between the first and second moderated signals; and determining whether the gas sensor is in the abnormal state on the basis of the deviation obtained during the diagnosis period.

16 Claims, 10 Drawing Sheets

DIAGNOSTIC METHOD AND APPARATUS FOR GAS SENSOR

BACKGROUND OF THE INVENTION

The present invention relates to diagnostic method and apparatus for a gas sensor, and particularly to diagnostic method and apparatus to diagnose whether a gas sensor for sensing an air-fuel ratio of exhaust gas is in an abnormal state or not.

There has been a gas sensor attached to an exhaust passage of an internal combustion engine such as an engine for a vehicle, and adapted to sense a concentration of a specific gas component included in an exhaust gas. A detection signal outputted by such a gas sensor (in detail, a sensor element constituting the gas sensor) is sent to an ECU (electronic control unit). The ECU is configured to detect an air-fuel ratio of the exhaust gas on the basis of the received detection signal, and thereby performs an air-fuel ratio feedback control to adjust an injection quantity of fuel for the engine and the like. As such a gas sensor, there is an oxygen sensor for sensing an oxygen concentration in the exhaust gas. Recently, a wide-band (full-range) air-fuel ratio sensor adapted to vary its sensor output value linearly according to the oxygen concentration in the exhaust gas has been used in order to achieve a more precise air-fuel ratio feedback control or the like.

In the case that the gas sensor has been used for a long time, there is a possibility that the gas sensor deteriorates with time. Namely for example, a gas-flow hole formed in a protector (in detail, a protector protecting the sensor element by covering a periphery of the sensor element) of the gas sensor or a porous portion guiding the exhaust gas into the sensor element is clogged. If the gas sensor causes such a deterioration, a response of sensor output value according to a variation of the concentration of the specific gas component in the exhaust gas is delayed as compared with a gas sensor which is in not-deteriorated state (i.e., in a normal state).

In the case where the gas sensor has caused such a deterioration, there is a fear that a reduction in operating performance of engine, a reduction in fuel economy, a reduction in cleaning performance of the exhaust gas, or the like is incurred. Hence, it is diagnosed whether or not the gas sensor is in an abnormal state on the basis of the detection signal of the gas sensor. Japanese Patent Application Publication No. H03(1991)-202767 corresponding to U.S. Pat. No. 5,052,361 discloses previously-proposed abnormality diagnostic method and apparatus. In this technique, a deviation between a detection signal outputted by a gas sensor to be diagnosed and a reference value preset outside a value range of a detection signal obtainable by a normal gas sensor is calculated. Then, by comparing the integral of this deviation with a judging value (deterioration reference value) defined as a criterion for deterioration diagnosis, it is diagnosed whether or not the gas sensor is in an abnormal state (deteriorated state).

In this Application Publication No. H03(1991)-202767, as the above reference value for calculating the deviation, two kinds of reference values are provided respectively for the case where a target air-fuel ratio for an air-fuel mixture is in a rich side and for the case where the target air-fuel ratio for the air-fuel mixture is in a lean side. In the normal (not-deteriorated) gas sensor, the value of the detection signal reverses to follow a reversal of the target air-fuel ratio, and varies to sequentially approach the reference value for the rich side and the reference value for the lean side. Accordingly, the deviation between the reference value and the value of detection signal is relatively small. On the other hand, in the gas sensor having some abnormality, the reversal of the detection signal is delayed relative to the reversal of the target air-fuel ratio. Accordingly, the deviation between the detection signal value and the reference value for the rich or lean side is relatively great. Therefore, when calculating the integral of the deviation, this integral has a magnitude according to a deterioration degree of the gas sensor. Thus, the abnormality diagnosis can be performed by comparing this integral of deviation with the deterioration reference value.

SUMMARY OF THE INVENTION

However, even if all the gas sensors have identical product number, the gas sensors include some sensors allowing those detection-signal values to rise or fall relative to an aim value (designed value) for those detection signals under a constant concentration of a specific gas component, namely cause so-called variations in individuals (manufacturing tolerance of sensor) to no small extent. Such a phenomenon that the detection-signal values of some gas sensors which are indicated when exposing the gas sensors under the identical concentration of specific gas component deviate from the aim value is also caused by variations in individuals of a sensor drive circuit section for driving the gas sensor. Accordingly, in the case where a reference value(s) for being compared with the detection signals to calculate the deviations is set at a fixed value as disclosed by the abnormality diagnostic method and apparatus in the above Application Publication No. H03 (1991)-202767, the calculated deviations are dispersed, i.e., take different values among respective gas sensors due to the variations in individuals even if the respective gas sensors are in the similar deterioration degree as one another. Accordingly, it has been difficult to say that the abnormality diagnosis can be performed with a high accuracy.

Therefore, it is an object of the present invention to provide gas sensor diagnostic method and/or apparatus devised to diagnose more accurately whether a gas sensor is in an abnormal state.

According to one aspect of the present invention, there is provided a gas sensor diagnostic method for diagnosing whether a gas sensor is in an abnormal state or not on the basis of a detection signal outputted by the gas sensor exposed in an exhaust gas exhausted from an internal combustion engine, the detection signal representing a concentration of a specific gas component in the exhaust gas, the gas sensor diagnostic method comprising: a target air-fuel-ratio reversal number counting step of counting the reversal number of times that a target air-fuel ratio for an air-fuel mixture to be supplied to the internal combustion engine reverses from a rich side to a lean side or from the lean side to the rich side through a specific air-fuel ratio defined as a boundary of the rich and lean sides; a detection signal obtaining step of obtaining the detection signal of the gas sensor at constant time intervals during a diagnosis period which is a period between a timing when the reversal number of times starts to be counted and a timing when the reversal number of times reaches a predetermined number of times; a moderated signal calculating step of calculating a first moderated signal by applying a first moderation calculation to the obtained detection signal, and a second moderated signal by applying a second moderation calculation different from the first moderation calculation, to the obtained detection signal; a deviation calculating step of calculating a deviation between the calculated first moderated signal and second moderated signal; and an abnormality diagnosing step of determining whether the gas sensor is in the abnormal state or not on the basis of the deviation obtained during the diagnosis period.

According to another aspect of the present invention, there is provided a gas sensor diagnostic apparatus adapted to diagnose whether a gas sensor is in an abnormal state or not on the basis of a detection signal outputted by the gas sensor exposed in an exhaust gas exhausted from an internal combustion engine, the detection signal representing a concentration of a specific gas component in the exhaust gas, the gas sensor diagnostic apparatus comprising: a target air-fuel-ratio reversal number counting section configured to count the reversal number of times that a target air-fuel ratio for an air-fuel mixture to be supplied to the internal combustion engine reverses from a rich side to a lean side or from the lean side to the rich side through a specific air-fuel ratio defined as a boundary of the rich and lean sides; a detection signal obtaining section configured to obtain the detection signal of the gas sensor at constant time intervals during a diagnosis period which is a period between a timing when the reversal number of times starts to be counted and a timing when the reversal number of times reaches a predetermined number of times; a moderated signal calculating section configured to calculate a first moderated signal by applying a first moderation calculation to the obtained detection signal, and a second moderated signal by applying a second moderation calculation different from the first moderation calculation, to the obtained detection signal; a deviation calculating section configured to calculate a deviation between the calculated first moderated signal and second moderated signal; and an abnormality diagnosing section configured to determine whether the gas sensor is in the abnormal state or not on the basis of the deviation obtained during the diagnosis period.

The other objects and features of this invention will become understood from the following description with reference to the accompanying drawings.

DETAILED DESCRIPTION OF THE INVENTION

Reference will hereinafter be made to the drawings in order to facilitate a better understanding of the present invention.

Figure 1:
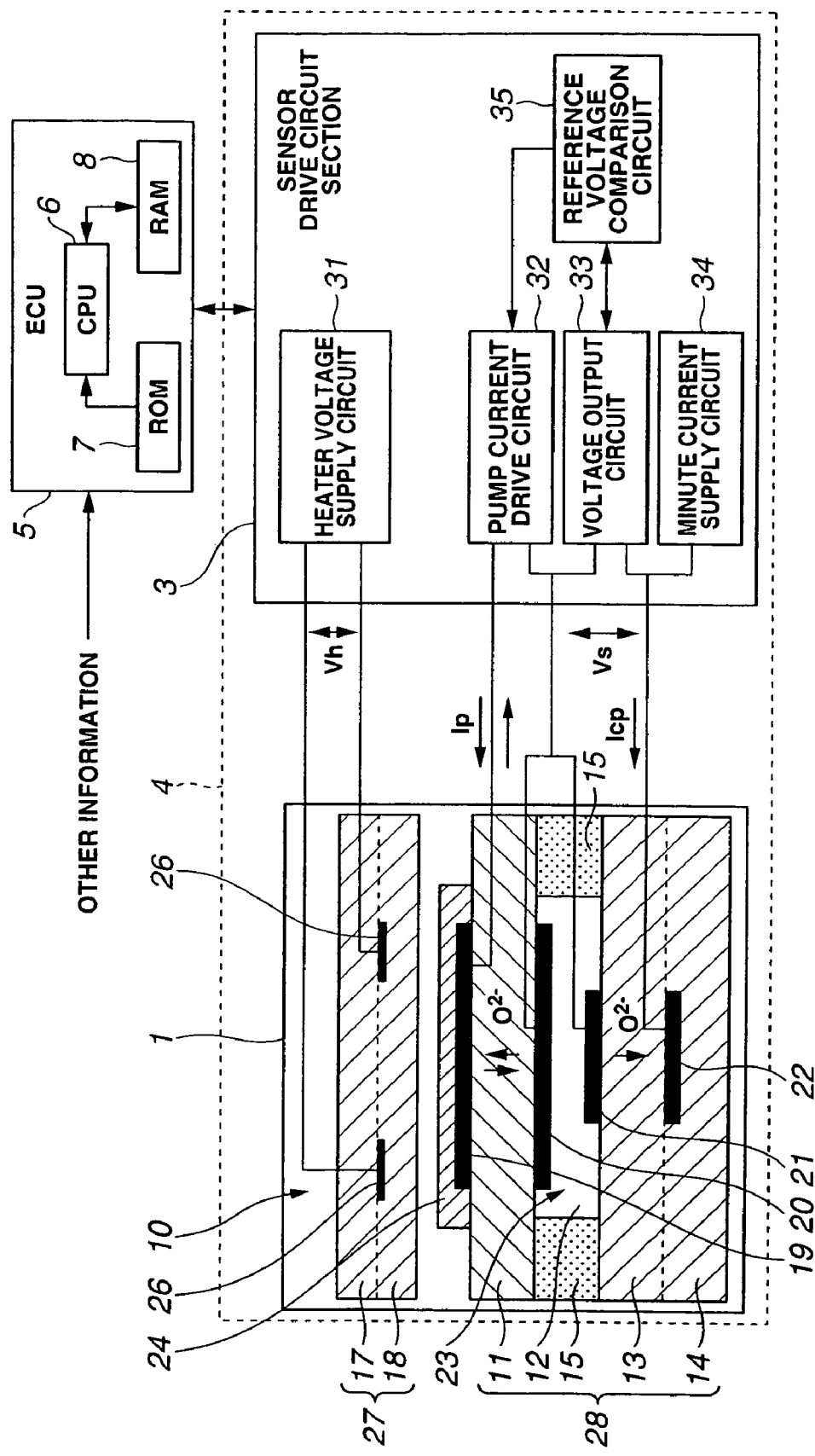
FIG. 1 is a schematic block diagram for explaining an electrical configuration between an ECU 5 and a wideband air-fuel ratio sensor 1.

An embodiment of abnormality diagnostic method and apparatus for a gas sensor according to the present invention will be explained referring to the drawings. At first, an abnormality diagnostic apparatus capable of achieving an abnormality diagnosis or diagnostic method for a gas sensor according to the present invention will be now explained with reference to FIG. 1. In this embodiment, an ECU (electronic control unit) 5 which is capable of judging (diagnosing) whether or not the gas sensor is in an abnormal state (improper state) on the basis of a detection signal outputted by the gas sensor is exemplified as the abnormality diagnostic apparatus. Moreover, a wideband (full-range) air-fuel ratio sensor 1 is exemplified as the gas sensor. FIG. 1 is a block diagram for explaining an electrical configuration between the ECU 5 and the wideband air-fuel ratio sensor 1.

In this embodiment, the case that a linking circuit-substrate (not shown) is interposed between the wideband air-fuel ratio sensor 1 and the ECU 5 to provide an after-mentioned sensor drive circuit section 3 as one circuit section arranged on the linking circuit-substrate will be explained as one example. However, the sensor drive circuit section 3 may be provided in the ECU 5 as one circuit section of ECU 5. Therefore, strictly speaking, "output of the gas sensor" according to the present invention corresponds to an output of a sensor unit 4 including the wideband air-fuel ratio sensor 1 and the sensor drive circuit section 3. However, for convenience sake, the following explanations of this embodiment are described by regarding the "output of the gas sensor" as an output of the wideband air-fuel ratio sensor 1.

The wideband air-fuel ratio sensor 1 shown in FIG. 1 is attached to an exhaust passage (not shown) of an engine of automotive vehicle, and is exposed in an exhaust gas (gas mixture) flowing through the exhaust passage. This wideband air-fuel ratio sensor 1 is a sensor serving to sense an air-fuel ratio of the exhaust gas on the basis of a concentration of a specific gas component, oxygen in this embodiment, included in the exhaust gas. The wideband air-fuel ratio sensor 1 internally includes a sensor element 10 formed in a long and narrow plate shape, and the sensor element 10 is held inside a housing (not shown) of the wideband air-fuel ratio sensor 1. Signal lines (wires) for getting the signal outputted by this sensor element 10 are led from the wideband air-fuel ratio sensor 1 toward the sensor drive circuit section 3, and then electrically connected with the sensor drive circuit section 3 on the linking circuit-substrate (not shown) disposed apart from the wideband air-fuel ratio sensor 1. The output of the sensor unit 4 including the wideband air-fuel ratio sensor 1 and the sensor drive circuit section 3 is inputted to the ECU 5 of the vehicle. The ECU 5 carries out an air-fuel ratio feedback control for the engine, on the basis of the output of sensor unit 4, i.e., the output of wideband air-fuel ratio sensor 1.

A structure of the sensor element 10 will be now explained. The sensor element 10 includes a detection member (detection body) 28 serving to detect an oxygen concentration of exhaust gas, and a heater member (heater body) 27 serving to heat the detection member 28. The detection member 28 includes an insulating base 12, and solid electrolyte plates or layers 11, 13 and 14. The detection member 28 has the structure of a laminate of the solid electrolyte layers 14 and 13, the insulating base 12 and the solid electrolyte layer 11 which are laminated in this order from bottom to top as viewed in FIG. 1. The solid electrolyte layers 11, 13 and 14 are formed mainly by using zirconia, and the insulating base 12 is formed mainly by using alumina. A pair of electrodes 19 and 20 are provided respectively on both upper and lower surfaces (i.e., on two opposite surfaces in a laminating direction) of the solid electrolyte layer 11. The pair of electrodes 19 and 20 are formed predominantly of platinum. Similarly, a pair of electrodes 21 and 22 are provided respectively on both upper and lower surfaces (on two opposite surfaces in the laminating direction) of the solid electrolyte layer 13. The electrode 22 is sandwiched between the solid electrolyte layers 13 and 14, and is buried in the solid electrolyte layers. Each of the insulating base 12 and the solid electrolyte layers 11, 13 and 14 is formed as a long and narrow plate body having a strip shape. FIG. 1 shows a cross section perpendicular to an extension direction (i.e., to a broadest plate-surface direction) of these plate bodies.

A gas sensing chamber 23 is provided on one end side of the insulating base 12 in the extension direction of the insulating base 12. Two surfaces of respective solid electrolyte layers 11 and 13 define wall surfaces of the gas sensing chamber 23 which are opposed in the laminating direction. The gas sensing chamber 23 is a hollow internal space (cavity) capable of introducing exhaust gas into the gas sensing chamber 23. At both end portions of this gas sensing chamber 23 in a width direction of the gas sensing chamber 23, porous diffusion-limited sections 15 are provided for controlling or limiting a gas inflow amount (rate) when introducing exhaust gas into the gas sensing chamber 23. The above-mentioned electrode 20 disposed on the solid electrolyte layer 11 and the electrode 21 disposed on the solid electrolyte layer 13 are respectively exposed to the gas sensing chamber 23.

The heater member 27 is formed predominantly of alumina. The heater member 27 includes two insulating bases 17 and 18, and heating resistors 26. Each of the two insulating bases 17 and 18 is in the form of a plate in the similar manner as the detection member 28. The heating resistors 26 are formed predominantly of platinum. The heater member 27 has the structure of a laminate of the two insulating bases 17 and 18 between which the heating resistors 26 are sandwiched and buried. Namely, the two insulating bases 17 and 18 are layered to surround the heating resistors 26 therebetween. It is known that a solid electrolyte formed of zirconia has an insulation property (quality) at ordinary temperatures, however has an oxygen-ion conductive property in a high-temperature environment. This is because the solid electrolyte formed of zirconia becomes activated in the high-temperature environment. The heater member 27 is provided in order to heat and activate the solid electrolyte layers 11, 13 and 14.

The heater member 27 is placed over an outside surface (layer) of the detection member 28 on the solid electrolyte layer 11's side of the detection member 28, so that the heater member 27 and the detection member 28 confront each other. A gap (space) within which gas can flow is formed between the insulating base 18 of heater member 27 and the solid electrolyte layer 11 of detection member 28. The electrode 19 placed on the solid electrolyte layer 11 is located in this gap, and is covered or enclosed by a porous protection layer 24. The protection layer 24 is formed of ceramic. The protection layer 24 covers a surface of the electrode 19 so as to protect the electrode 19 from deteriorating due to a poisoning component such as a silicon included in the exhaust gas.

In the sensor element 10 constructed as mentioned above, the solid electrolyte layer 11 and the pair of electrodes 19 and 20 provided on the both surfaces of the solid electrolyte layer 11 in the laminating direction function as an oxygen pumping cell for pumping oxygen into the gas sensing chamber 23 from the external and for pumping out oxygen from the gas sensing chamber 23 to the external (hereinafter, the solid electrolyte layer 11 and the electrodes 19 and 20 are also collectively called "Ip cell"). Similarly, the solid electrolyte layer 13 and the pair of electrodes 21 and 22 provided on the both surfaces of layer 13 in the laminating direction function as an oxygen concentration sensing cell for producing an electromotive force in accordance with oxygen concentration between the both electrodes 21 and 22 (hereinafter, the solid electrolyte layer 13 and the electrodes 21 and 22 are also collectively called "Vs cell"). Moreover, the electrode 22 functions as an oxygen reference electrode which maintains a reference oxygen concentration for being used for the detection of oxygen concentration within the gas sensing chamber 23. Detailed explanations about the functions of "Ip cell" and "Vs cell" will be described later.

Next, the structure of the sensor drive circuit section 3 connected with the sensor element 10 will be now explained. The sensor drive circuit section 3 includes a heater voltage supply circuit 31, a pump current drive circuit 32, a voltage output circuit 33, a minute current supply circuit 34 and a reference voltage comparison circuit 35. The sensor drive circuit section 3 is an electrical circuit section for obtaining an electric-current value according to the oxygen concentration of exhaust gas from the sensor element 10, as a voltage signal. As mentioned above, it is noted that this sensor drive circuit section 3 may be provided as one circuit section of the aftermentioned ECU 5.

The heater voltage supply circuit 31 applies a voltage Vh across both terminals of each heating resistor 26 in the heater member 27 of sensor element 10, and thereby heats the heating resistors 26 so that the Ip cell and Vs cell are heated. The minute current supply circuit 34 passes or applies a minute electric-current Icp from the side of electrode 22 to the side of electrode 21 in the Vs cell, and thereby moves oxygen ion to the side of electrode 22 so that oxygen is stored or held in the side of electrode 22. Thereby, the electrode 22 is made to function as the oxygen reference electrode which is the reference for sensing the concentration of oxygen contained in the exhaust gas. The voltage output circuit 33 is a circuit to sense an electromotive force Vs generated between the electrodes 21 and 22 of the Vs cell. The reference voltage comparison circuit 35 is configured to compare a predetermined reference voltage (for example, 450 mV) with the electromotive force Vs sensed by the voltage output circuit 33, and feed the result of the comparison back to the pump current drive circuit 32 for a feedback control. In accordance with the comparison result fed back from the reference voltage comparison circuit 35, the pump current drive circuit 32 controls a pump current Ip passing between the electrodes 19 and 20 of the Ip cell. Thereby, the pump current drive circuit 32 allows the Ip cell to pump (move) oxygen into the gas sensing chamber 23 or to pump out (move) oxygen from the gas sensing chamber 23.

Next, the structure of the ECU 5 will be now explained. The ECU 5 is a unit for electronically controlling a drive of the engine of vehicle and the like. The ECU 5 is configured to control a fuel injection timing, an ignition timing and the like in accordance with executions of control programs. As the information for such programs, the output (detection signal) of wideband air-fuel ratio sensor 1 is inputted to the ECU 5. The ECU 5 also receives the signals from the other sensors as the other information (e.g., a crank angle signal capable of giving a piston position and a rotational speed of the engine, a temperature signal of cooling water, a combustion pressure signal, and the like). The ECU 5 includes a microcomputer chip equipped with a CPU 6, a ROM 7, a RAM 8 and the like which have known structures. The output (detection signal) corresponding to the oxygen concentration of exhaust gas which is obtained through a signal input/output section (not shown) from the sensor drive circuit section 3 of sensor unit 4 is converted to a digital value by way of analog-digital conversion, and then stored in the RAM 8. This stored value is used in an after-mentioned abnormality diagnosing program.

Figure 2:
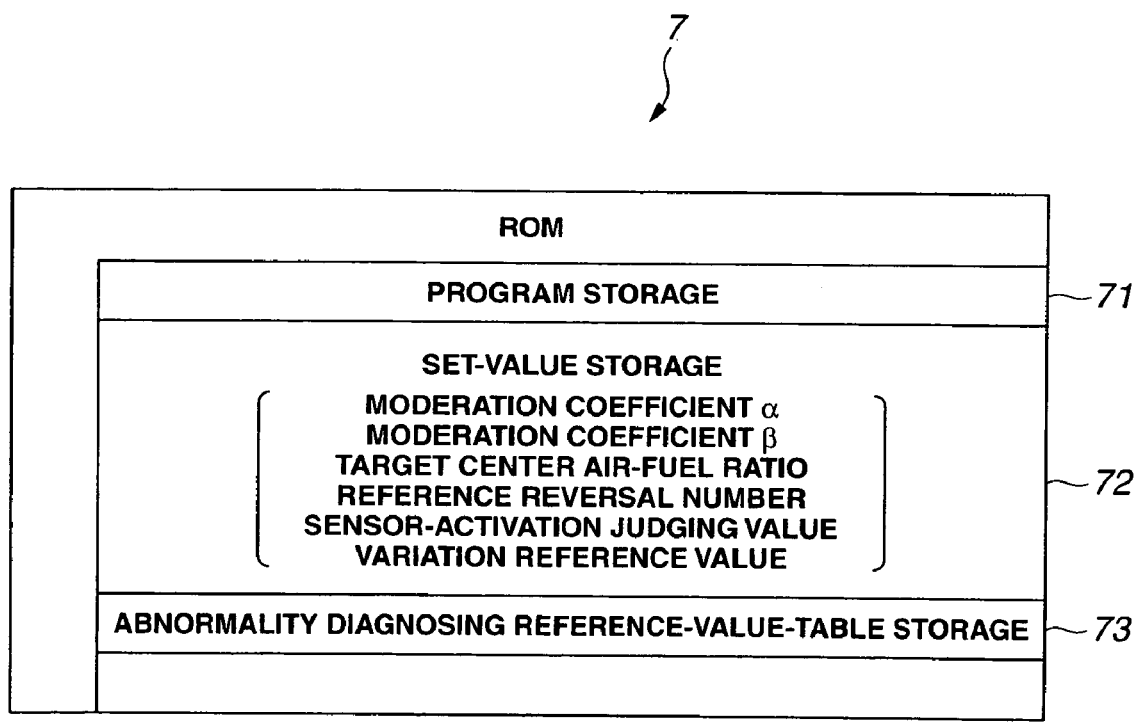
FIG. 2 is a conceptual diagram showing a configuration of storage areas of a ROM 7.
Figure 3:
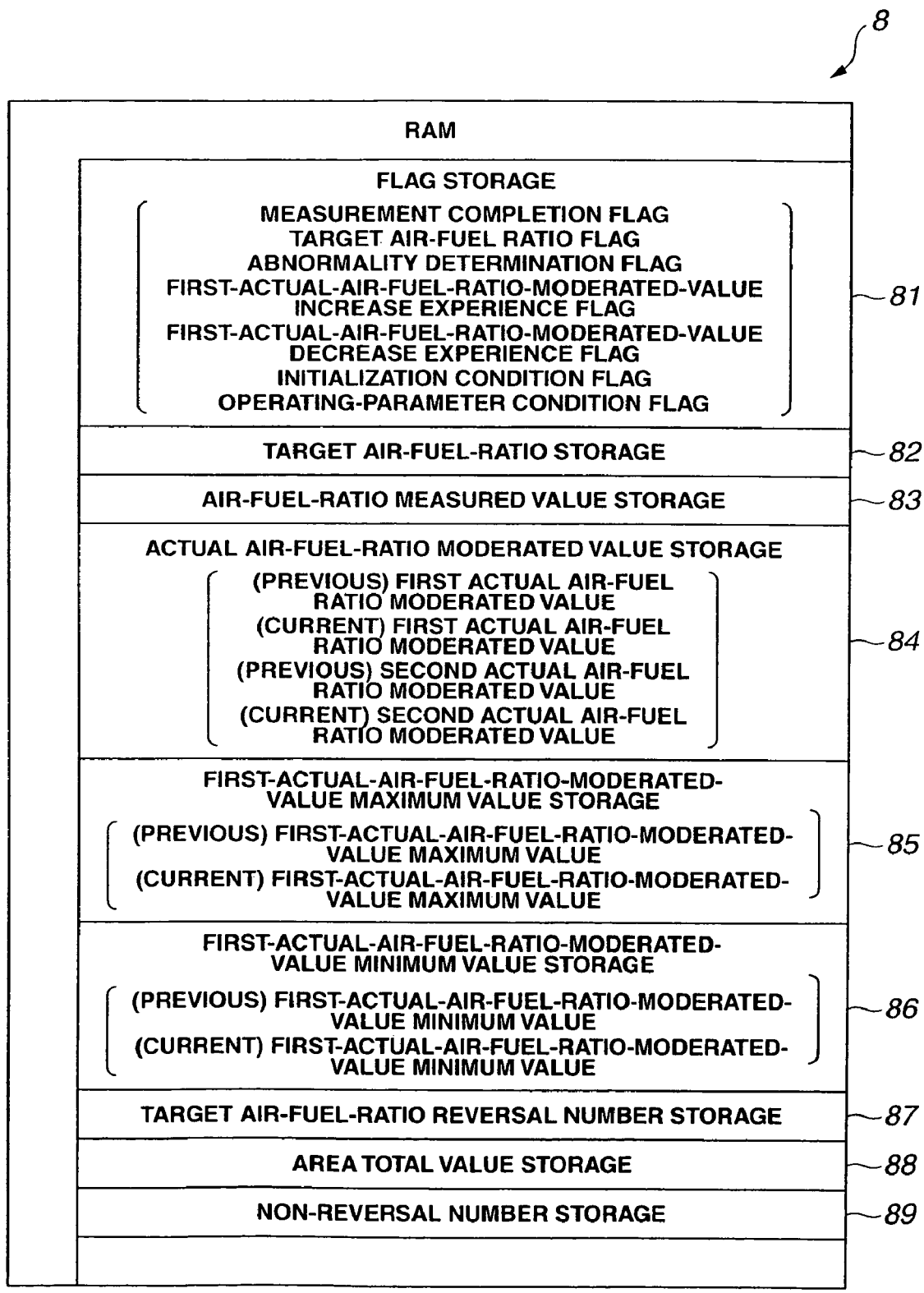
FIG. 3 is a conceptual diagram showing a configuration of storage areas of a RAM 8.

In this embodiment, the ECU 5 determines whether or not the sensor element 10 is in an abnormal state, by executing the after-mentioned abnormality diagnosing program on the basis of the output values derived from the wideband air-fuel ratio sensor 1. The abnormality diagnosing program has been stored in ROM 7, and is executed by the CPU 6. Storage areas in ROM 7 and RAM 8 are now explained with reference to FIGS. 2 and 3. FIG. 2 is a conceptual diagram showing a configuration of storage areas (memory areas) of the ROM 7. FIG. 3 is a conceptual diagram showing a configuration of storage areas of the RAM 8.

In addition to the after-mentioned abnormality diagnosing program, various control programs, initial values (default values) and the like have been stored in the ROM 7. As shown in FIG. 2, the storage areas of ROM 7 related to the abnormality diagnosing program include a program storage area 71, a set-value storage area 72, an abnormality diagnosing reference-value-table storage area 73, and the like.

The program storage area 71 is configured such that various programs including the abnormality diagnosing program are stored in the program storage area 71. Initial values, set values and the like which are used during the execution of abnormality diagnosing program have been stored in the set-value storage area 72. Specifically, the set-value storage area 72 memorizes moderation coefficients α and β (respectively corresponding to "first moderation coefficient" and "second moderation coefficient" according to the present invention, for example, α=0.9 and β=0.2) which are used when calculating first and second actual air-fuel-ratio moderated values during execution of an after-mentioned response-delay diagnosis processing of the abnormality diagnosing program; and memorizes a target center air-fuel ratio (corresponding to "specific air-fuel ratio" according to the present invention, for example, 14.6 in the case that a theoretical air-fuel ratio is employed as a boundary) which is the boundary (reference value) for determining whether a target air-fuel ratio of air-fuel mixture is in a rich region or in a lean region. Moreover in this embodiment, from a time point when the target air-fuel ratio of air-fuel mixture enters the lean region from the rich region (i.e., from a time point of reverse of the target air-fuel ratio from rich side to lean side), the number of reversals is counted by being incremented by 1 every time the target air-fuel ratio reverses or enters from in the rich side to in the lean side (hereinafter, this every time-period is referred to as "unit diagnosis period"). A time duration necessary for the counted number of reversals to reach a predetermined reference reversal number (for example, 5 times) is defined as a diagnosis period during which the outputs of the wideband air-fuel ratio sensor 1 are obtained for the abnormality diagnosis. Namely, the outputs of the wideband air-fuel ratio sensor 1 are used for the abnormality diagnosis during the time duration between the time point when the target air-fuel ratio of air-fuel mixture has just entered the lean region from the rich region and the time point when the number of times of repeated reversals (entrances) in the target air-fuel ratio has just reached the predetermined reference reversal number. The predetermined reference reversal number for determining this diagnosis period has been also stored in the set-value storage area 72.

Moreover, a sensor-activation judging value and a variation reference value (e.g., 0.02 V) have been also stored in the set-value storage area 72. The sensor-activation judging value is a reference value which is used when judging whether or not the wideband air-fuel ratio sensor 1 has been already activated in order to judge whether or not a start condition for the abnormality diagnosis has been satisfied. The variation reference value is a reference value for being compared when judging whether the calculated first actual air-fuel-ratio moderated value is in an increasing state or in a decreasing state.

Moreover, a plurality of abnormality diagnosing reference values have been stored in the abnormality diagnosing reference-value-table storage area 73. Each of the abnormality diagnosing reference values is a reference value (criterion) for being compared when judging or diagnosing whether the wideband air-fuel ratio sensor 1 is in the abnormal state. In this embodiment, the abnormality diagnosing reference value is changed or selected in accordance with a variation state (variation history) of the first actual air-fuel-ratio moderated value during the diagnosis period. Specifically, the abnormality diagnosing reference value is changed in accordance with the number (non-reversal number) which is obtained by counting or summing, for the (whole) diagnosis period, the number of times that the first actual air-fuel-ratio moderated value could not follow the reversals of target air-fuel ratio and thereby could not reverse during the unit diagnosis period.

The ECU 5 carries out the feedback correction based on the output of wideband air-fuel ratio sensor 1 to bring the air-fuel ratio (actual air-fuel ratio) closer to the target air-fuel ratio. At that time, depending on a progression degree of deterioration in the wideband air-fuel ratio sensor 1, there is the case where the feedback correction is excessively carried out. When such a situation is repeated, the detection signal of wideband air-fuel ratio sensor 1 to be outputted becomes greater (in amplitude). Accordingly, there is a possibility that a difference between the first and second actual air-fuel-ratio moderated values does not become small even though the deterioration of wideband air-fuel ratio sensor 1 has progressed. In this case, there is a possibility that the wideband air-fuel ratio sensor 1 cannot be properly distinguished from the not-deteriorated state (normal state) thereof. Therefore, in this embodiment, the abnormality diagnosing reference value is changed according to the non-reversal number. Thereby, the abnormality diagnosis for the wideband air-fuel ratio sensor 1 can be accurately achieved regardless of the progressing state of deterioration in the wideband air-fuel ratio sensor 1, i.e., even if the diagnosis period for the abnormality diagnosis is applied to any timing relative to the deterioration degree of wideband air-fuel ratio sensor 1. Specifically, the abnormality diagnosing reference values assigned to the non-reversal numbers (i.e., mapping table between the abnormality diagnosing reference value and the non-reversal number) have been stored in the abnormality diagnosing reference-value-table storage area 73. For example, this mapping table is provided in a manner that one of the abnormality diagnosing reference values is selected as follows. That is, the abnormality diagnosing reference value takes a value equal to 5 when the non-reversal number (of times) is equal to 0 or 1, the abnormality diagnosing reference value takes a value equal to 8 when the non-reversal number is equal to 2 or 3, the abnormality diagnosing reference value takes a value equal to 13 when the non-reversal number is equal to 4, and the abnormality diagnosing reference value takes a value equal to 18 when the non-reversal number is equal to 5. Moreover, the ROM 7 includes further various storage areas (not shown). It is noted that the non-reversal number (of times) corresponds to "non-transition number" according to the present invention.

Next, storage areas of the RAM 8 will be now explained. As shown in FIG. 3, the storage areas of RAM 8 related to the abnormality diagnosing program include a flag storage area 81, a target air-fuel ratio storage area 82, an air-fuel-ratio measured value storage area 83, an actual air-fuel-ratio moderated value storage area 84, a first-actual-air-fuel-ratio-moderated-value maximum value storage area 85, a first-actual-air-fuel-ratio-moderated-value minimum value storage area 86, a target air-fuel-ratio reversal number storage area 87, an area total value storage area 88, a non-reversal number storage area 89 and the like.

(After-mentioned) Some flags which are used during the execution of the abnormality diagnosing program are temporarily stored in the flag storage area 81. In the CPU 6, a program(s) for controlling the injection timing and injection quantity of fuel is executed separately from the abnormality diagnosing program. In such program(s) for controlling the injection, an air-fuel ratio targeted for the air-fuel mixture has been determined according to the operating state of the engine. This target air-fuel ratio read out from a storage area used in such program(s) is stored in the target air-fuel ratio storage area 82.

A result of applying analog-to-digital conversion to the pump current Ip passed through the Ip cell is stored in the air-fuel-ratio measured value storage area 83 from the sensor drive circuit section 3, as the output of the wideband air-fuel ratio sensor 1, namely, as an air-fuel ratio measured value. Two kinds of the (current) actual air-fuel ratio moderated values (current first and second actual air-fuel-ratio moderated values) and two kinds of the (previous) actual air-fuel ratio moderated values (previous first and second actual air-fuel-ratio moderated values) are stored in the actual air-fuel-ratio moderated value storage area 84. Each of the (current) actual air-fuel ratio moderated values is obtained by applying a moderation calculation to the air-fuel ratio measured value during the execution of response-delay diagnosis processing. Each of the (previous) actual air-fuel ratio moderated values has been obtained during the previous (last-time) execution of response-delay diagnosis processing. Specifically, the (current) first actual air-fuel-ratio moderated value is calculated by applying the moderation calculation given by the following formula ① to the (current) air-fuel ratio measured value obtained as the output (detection signal) of the wideband air-fuel ratio sensor 1 and the (previous) first actual air-fuel ratio moderated value calculated in the previous (last-time) moderation calculation, with the use of the first moderation coefficient α. Namely, the (current) first actual air-fuel ratio moderated value is calculated by moderating or smoothing the (current) air-fuel ratio measured value at a constant rate given by the first moderation coefficient α.

(current) first actual air-fuel ratio moderated value=α×
air-fuel ratio measured value+(1−α)×(previous)
first actual air-fuel ratio moderated value     ① where, 0<α<1, for example, α=0.9 in this embodiment

In the same manner, the (current) second actual air-fuel-ratio moderated value is calculated by applying a moderation calculation given by the following formula ② to the (current) air-fuel ratio measured value, with the use of the second moderation coefficient β.

(current) second actual air-fuel ratio moderated
value=β×air-fuel ratio measured value+(1−β)×
(previous) second actual air-fuel ratio moderated
value     ② where, 0≦β≦1, for example, β=0.2 in this embodiment

As mentioned above, the first actual air-fuel ratio moderated value and the second actual air-fuel-ratio moderated value, namely the two kinds of actual air-fuel ratio moderated values are calculated by applying the moderation calculation using the moderation coefficients different from each other, to the (current) air-fuel ratio measured value. Thus, the current value and the previous (last-time) value of each of the first actual air-fuel ratio moderated value and the second actual air-fuel-ratio moderated value are stored in the actual air-fuel-ratio moderated value storage area 84.

Moreover, the maximum value of first actual air-fuel ratio moderated value within the unit diagnosis period which is given between adjacent two reversals (adjacent reversal timings) of the target air-fuel ratio from rich side to lean side is stored in the first-actual-air-fuel-ratio-moderated-value maximum value storage area 85. This maximum value is updated by comparing a previous (last-time) maximum value with the current first actual air-fuel ratio moderated value. Then, this maximum value is reset when the target air-fuel ratio moves (or makes a transition) from the rich side to the lean side. Moreover, the minimum value of first actual air-fuel ratio moderated value which is stored in the first-actual-air-fuel-ratio-moderated-value minimum value storage area 86 is updated in the same manner as the maximum value of first actual air-fuel ratio moderated value.

In this embodiment, the number of times of transitions (reversals) from rich side into lean side in the target air-fuel ratio repeatedly moving between in the rich side and in the lean side through the target center air-fuel ratio defined as the boundary of the rich and lean sides is counted up. Namely, this reversal (transition) number is increased by one when the target air-fuel ratio has just moved into the lean side from the rich side. This reversal number is stored in the target air-fuel-ratio reversal number storage area 87. An area total value is stored in the area total value storage area 88. This area total value is an integral of the absolute value of a difference between the first actual air-fuel ratio moderated value and the second actual air-fuel ratio moderated value. In other words, a lot of absolute values of the differences between the first actual air-fuel ratio moderated values and the second actual air-fuel ratio moderated values which have been obtained in current and earlier time-around calculations are added to one another to calculate the area total value. In this embodiment, the absolute value of the difference between the first actual air-fuel ratio moderated value and the second actual air-fuel ratio moderated value is called "deviation". The above-mentioned non-reversal number (the number of times that the first actual air-fuel ratio moderated value could not follow the reversals of target air-fuel ratio and thereby did not reverse during the diagnosis period) counted during the (whole) diagnosis period is stored in the non-reversal number storage area 89. Furthermore, the RAM 8 includes further various storage areas (not shown). It is noted that the area total value corresponds to "deviation total value" according to the present invention.

In the above-mentioned flag storage area 81, a measurement completion flag, a target air-fuel ratio flag, an abnormality determination flag, a first-actual-air-fuel-ratio-moderated-value increase experience flag, a first-actual-air-fuel-ratio-moderated-value decrease experience flag, an initialization condition flag, an operating-parameter condition flag and the like are stored. The measurement completion flag is set when the abnormality diagnosis for gas sensor has been just completed. The abnormality diagnosing program according to this embodiment is configured to perform the abnormality diagnosis for gas sensor only once during a time period between the drive start and drive stop of engine. It is judged whether or not each process for the abnormality diagnosis should be carried out, by using the above-mentioned measurement completion flag, the operating-parameter condition flag and the initialization condition flag.

The target air-fuel ratio flag is set according to the result of determining whether the target air-fuel ratio stored in the target air-fuel ratio storage area 82 falls within the rich region (side) or the lean region. Specifically, in the case where it is determined that the target air-fuel ratio is in the rich region by comparing the target air-fuel ratio with the target center air-fuel ratio stored in the set-value storage area 72, the target air-fuel ratio flag is set or stored at 1. On the other hand, in the case where it is determined that the target air-fuel ratio is in the lean region, the target air-fuel ratio flag is set at 0. The abnormality determination flag is set when the abnormality diagnosing program has diagnosed (determined) the gas sensor as the abnormal state. The status value of the abnormality determination flag is referred to (is read out) by the other program(s) executed by the CPU 6. Specifically, if the status value of the abnormality determination flag is 1, for example, a process for informing a driver of the abnormal state of wideband air-fuel ratio sensor 1 is carried out by the other program(s).

The first-actual-air-fuel-ratio-moderated-value increase experience flag is set when it is judged that the variation state of first actual air-fuel-ratio moderated value is in the increasing state during the unit diagnosis period. The first-actual-air-fuel-ratio-moderated-value decrease experience flag is set when it is judged that the variation state of first actual air-fuel-ratio moderated value is in the decreasing state during the unit diagnosis period. These first-actual-air-fuel-ratio-moderated-value increase experience flag and first-actual-air-fuel-ratio-moderated-value decrease experience flag are referred to (are read out) when conducting the counting of non-reversal number every unit diagnosis period (at every end timing of unit diagnosis period), and then, these first-actual-air-fuel-ratio-moderated-value increase experience flag and first-actual-air-fuel-ratio-moderated-value decrease experience flag are reset every unit diagnosis period.

The initialization condition flag is set when starting the abnormality diagnosing program, or is set as needed basis by a control program(s) other than the abnormality diagnosing program, in order to enable the response-delay diagnosis processing for gas sensor. For example, when the engine is started by turning on an ignition key of vehicle from its off state; the abnormality diagnosing program is executed so that the initialization condition flag is set or stored at 1, and thereby the response-delay diagnosis processing is carried out. After a first-time entire execution of the response-delay diagnosis processing has been finished, the abnormality diagnosing program becomes in a standby state. Under this standby state, for example when the engine is unexpectedly deactivated (so-call engine stall); the initialization condition flag is also set at 1 by the other control program(s) so that the response-delay diagnosis processing is again carried out.

The operating-parameter condition flag is also set by a control program(s) other than the abnormality diagnosing program. The running state of a whole system around the engine is monitored by the other control program(s) executed in the CPU 6. For example, if each value of the engine rotational speed and the cooling water temperature or the like remains for a predetermined time period (for example, 1 second) within a predetermined range regarded as its normal level; it is determined that the operating state of engine is normal (proper) and thus the operating-parameter condition flag is set at 1. In this embodiment, the range (condition) regarded as the normal level of engine rotational speed is between 2000 rpm and 5000 rpm (revolutions per minute), and the range regarded as the normal level of cooling water temperature is between 80° C. and 215° C.

Next, operations for detecting the oxygen concentration (air-fuel ratio) of exhaust gas by using the wideband air-fuel ratio sensor 1 are now briefly explained. At first, as shown in FIG. 1, the minute current supply circuit 34 supplies the minute electric-current Icp in a direction toward the electrode 21 from the electrode 22 of the Vs cell. By this current supply, oxygen is drawn (moved) to the side of electrode 22 from the side of electrode 21 through the solid electrolyte layer 13, and thereby the electrode 22 is made to function as the oxygen reference electrode. Then, the voltage output circuit 33 senses the electromotive force Vs generated between the both electrodes 21 and 22, and then the reference voltage comparison circuit 35 compares this electromotive force Vs with the reference voltage (for example, 450 mV). The pump current drive circuit 32 controls a magnitude and a direction of the pump current Ip flowing between the electrodes 19 and 20 of the Ip cell so as to cause the electromotive force Vs to become equal to the reference voltage, on the basis of the comparison result of the reference voltage comparison circuit 35.

In the case where the air-fuel ratio of exhaust gas guided into the gas sensing chamber 23 is rich (as compared to its reference value); the concentration of oxygen contained in exhaust gas is lean, therefore the pump current Ip flowing between the electrodes 19 and 20 is controlled to cause the Ip cell to draw (pump) oxygen from the external into the gas sensing chamber 23. On the other hand, in the case where the air-fuel ratio of exhaust gas guided into the gas sensing chamber 23 is lean; a lot of oxygen exists in exhaust gas, therefore the pump current Ip flowing between the electrodes 19 and 20 is controlled to cause the Ip cell to draw (pump out) oxygen to the external from the gas sensing chamber 23. The value of pump current Ip indicated at this time is outputted to the ECU 5 as the output (the air-fuel ratio measured value) of the wideband air-fuel ratio sensor 1. Accordingly, the ECU 5 can detect the oxygen concentration of exhaust gas and thereby the air-fuel ratio of exhaust gas, from the magnitude and direction of the pump current Ip.

Figure 4:
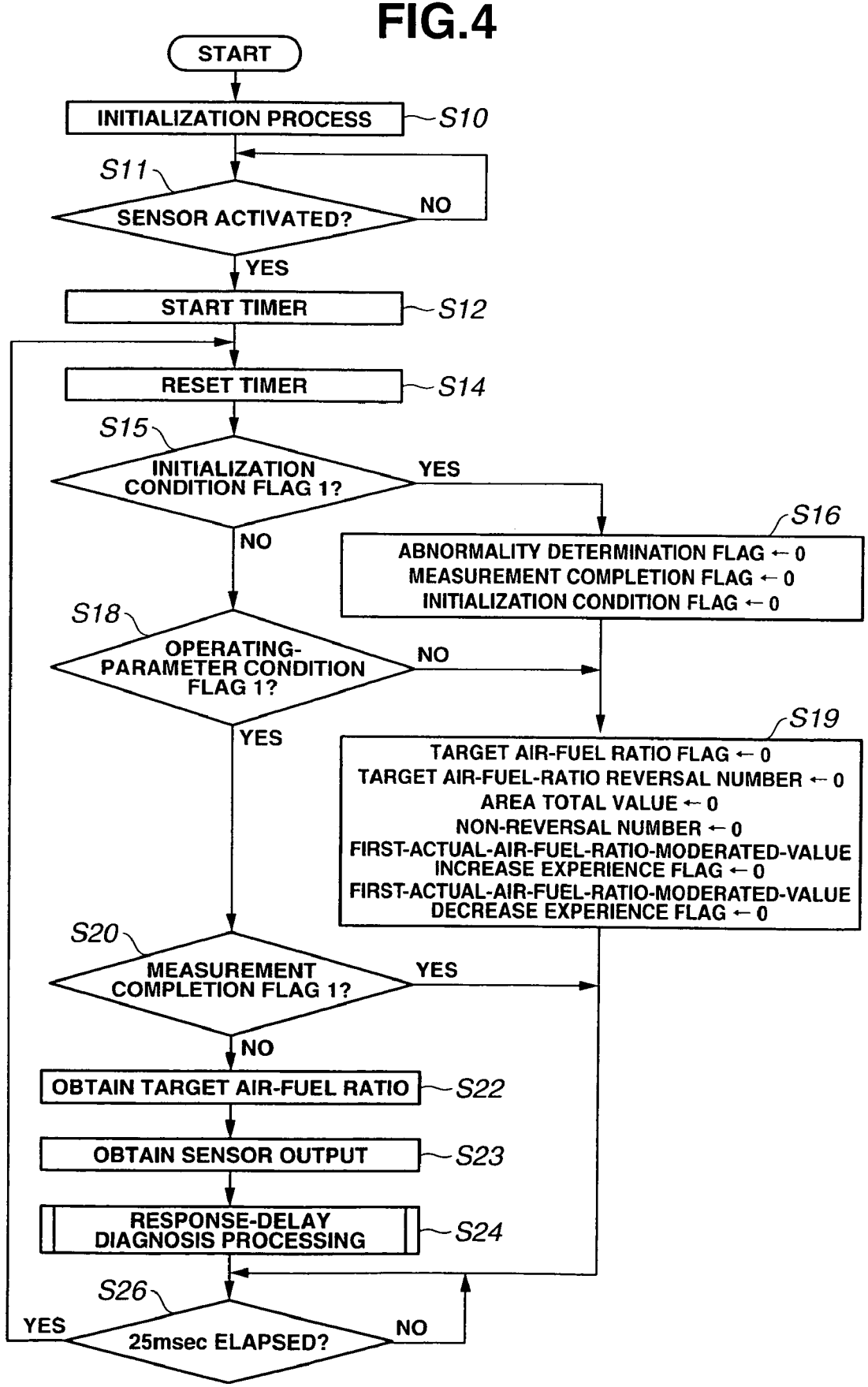
FIG. 4 is a flowchart showing a main routine of an abnormality diagnosing program.
Figure 5:
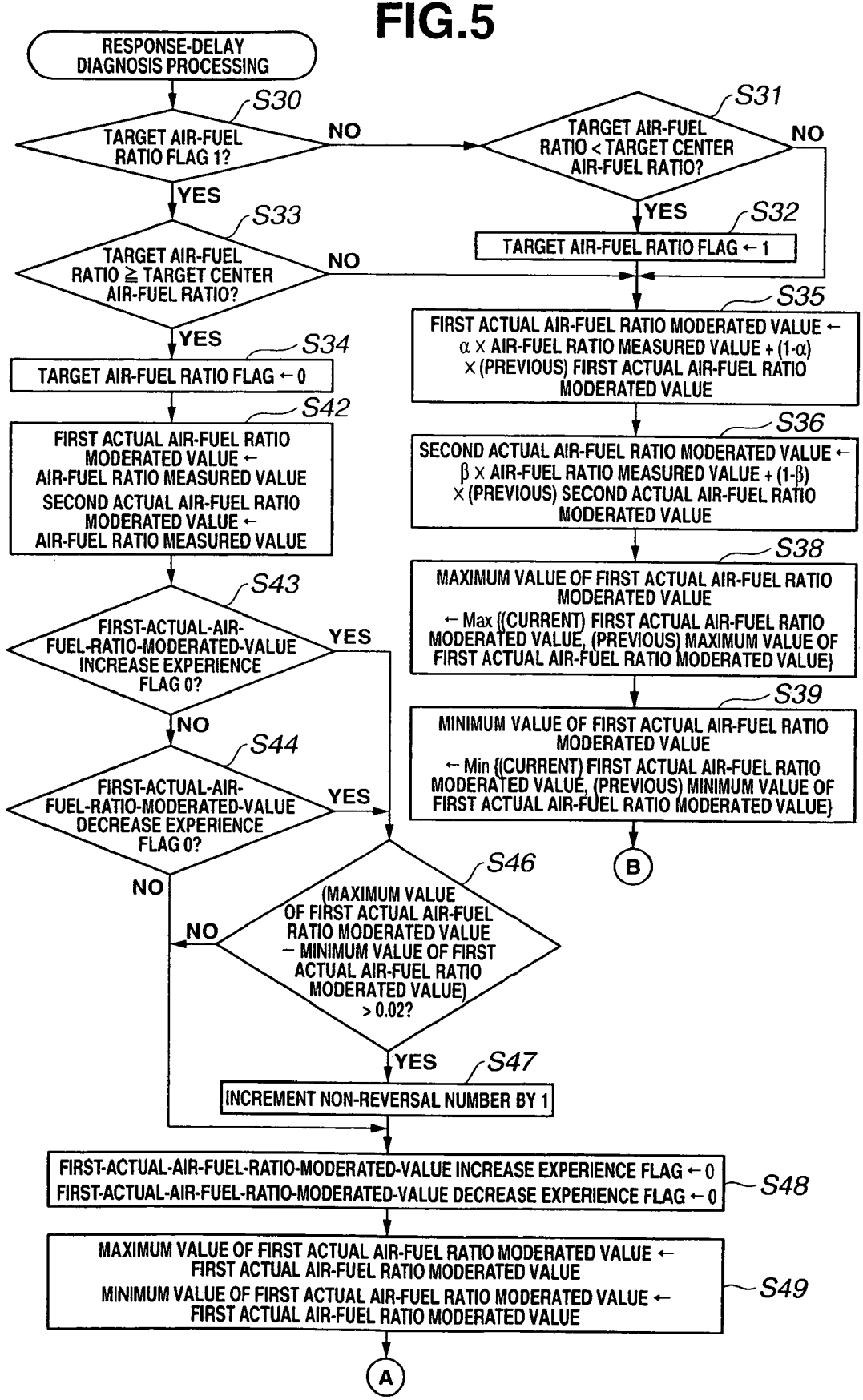
FIG. 5 is a flowchart showing a response-delay diagnosis processing which is called by the main routine of the abnormality diagnosing program.
Figure 6:
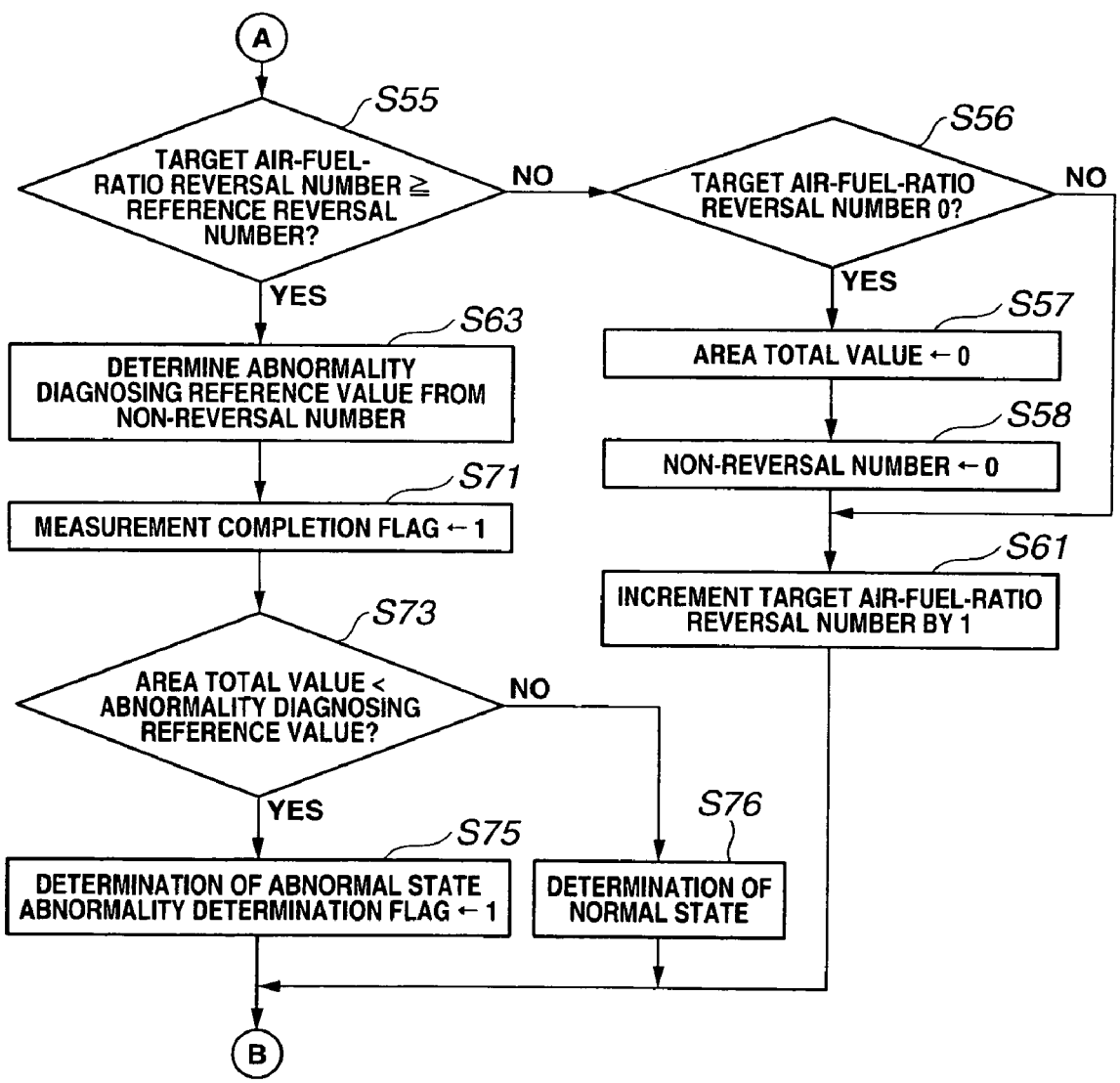
FIG. 6 is a flowchart showing the response-delay diagnosis processing which is called by the main routine of the abnormality diagnosing program.
Figure 7:
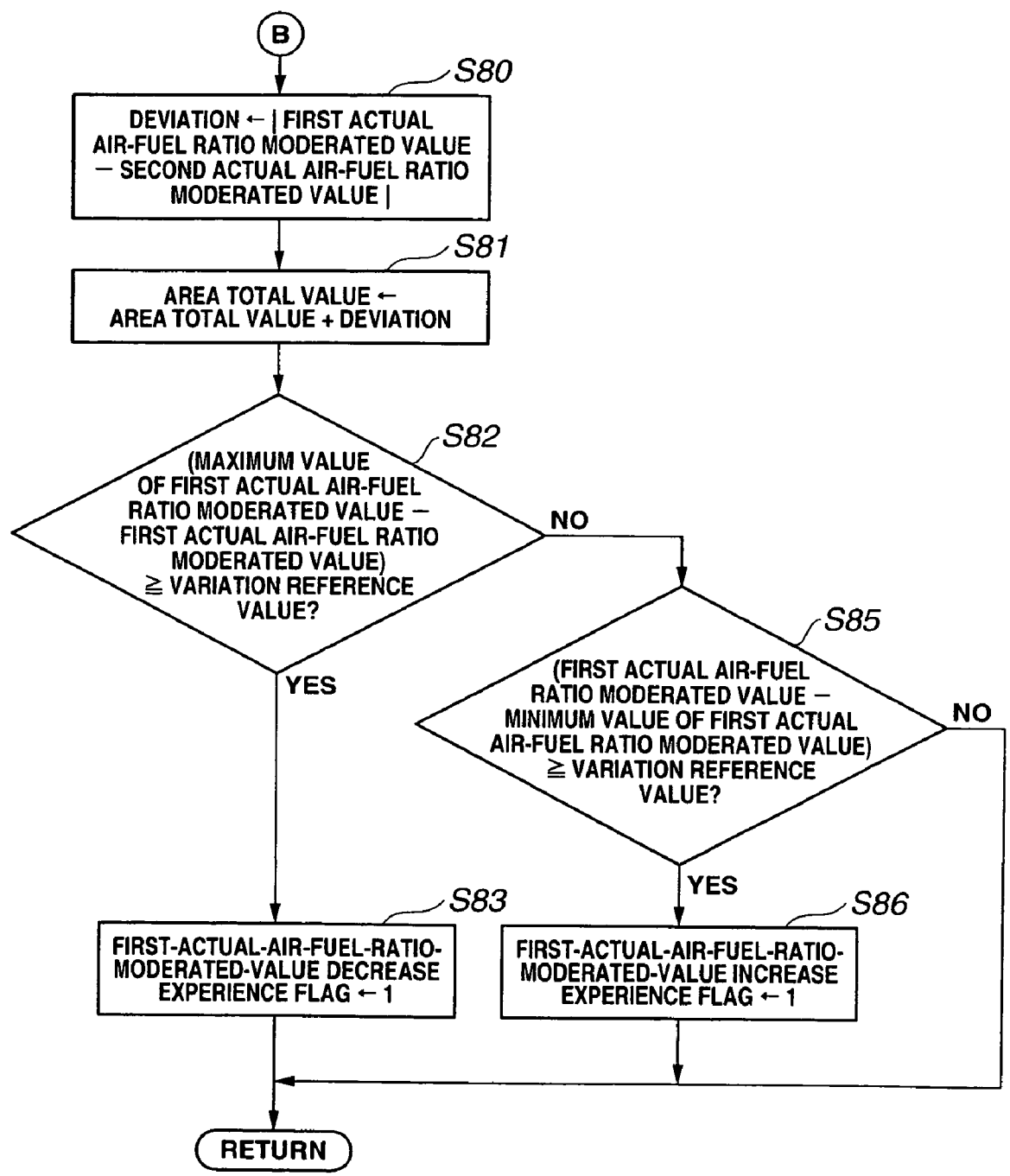
FIG. 7 is a flowchart showing the response-delay diagnosis processing which is called by the main routine of the abnormality diagnosing program.
Figure 8:
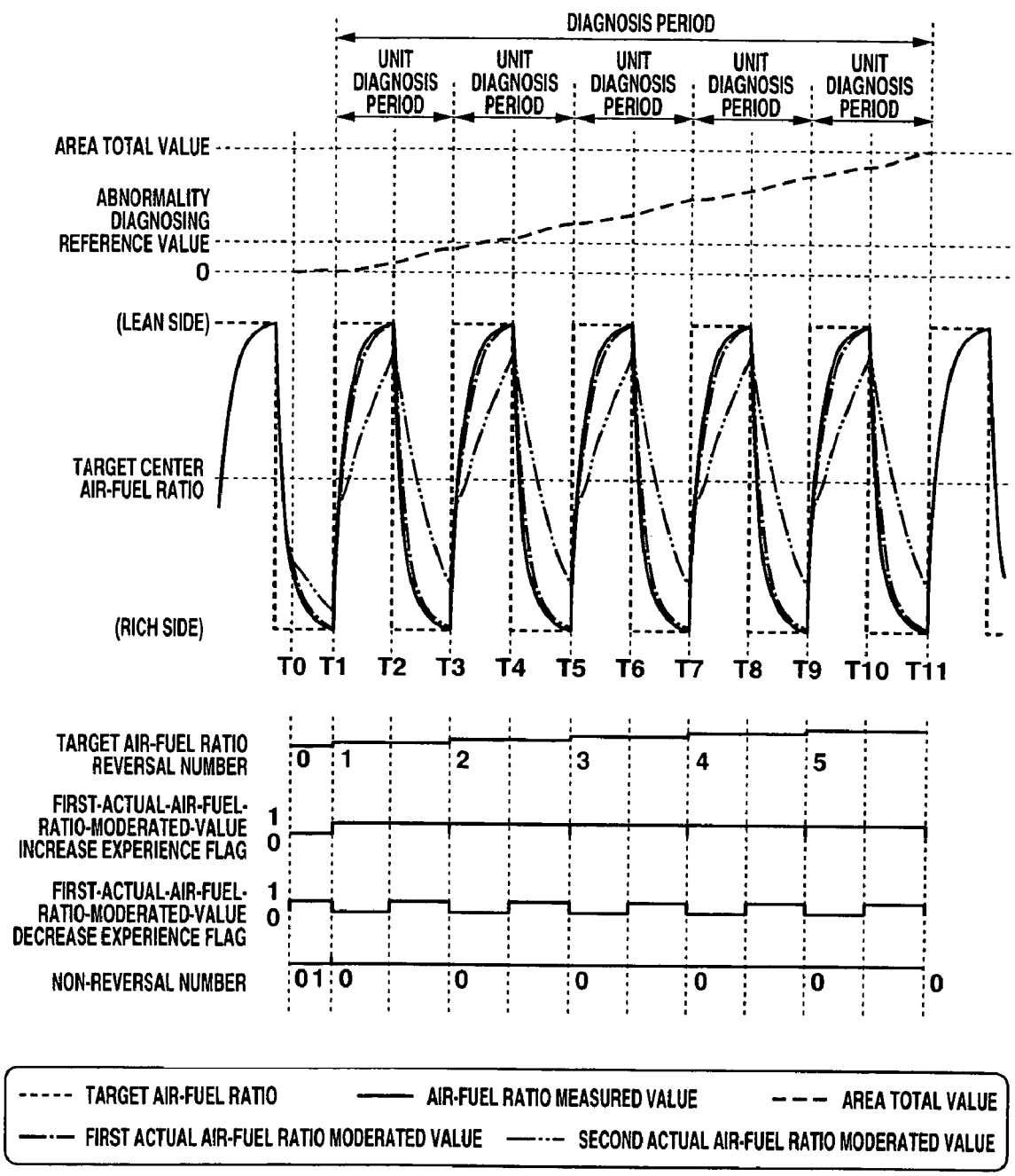
FIG. 8 is a timing chart showing one example of the appearance that an air-fuel ratio measured value varies by following the reversals of a target air-fuel ratio in the case where the gas sensor is not in abnormal state.
Figure 9:
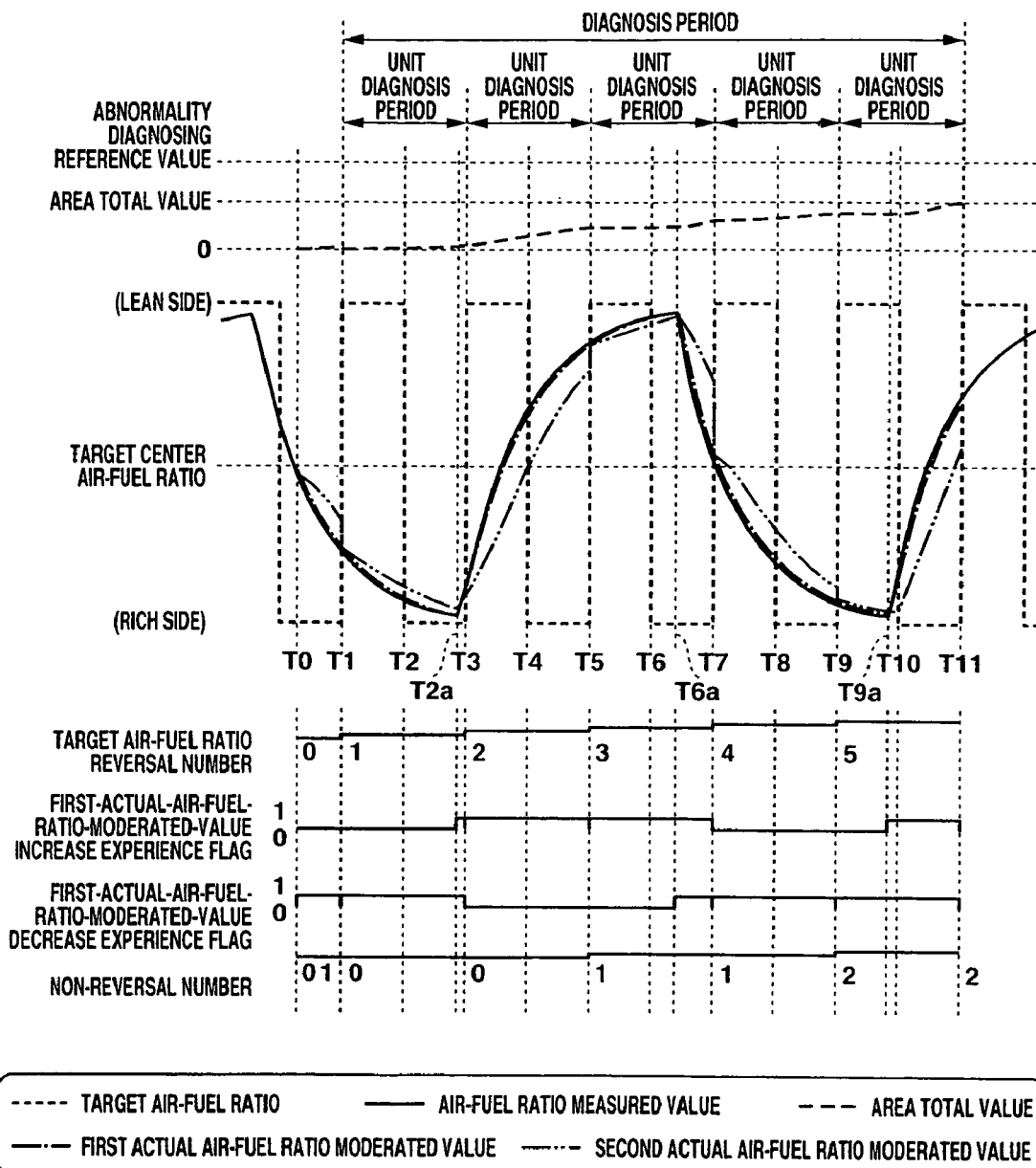
FIG. 9 is a timing chart showing one example of the appearance that the air-fuel ratio measured value varies with delay by failing to follow the reversals of the target air-fuel ratio in the case where the gas sensor is in the abnormal state.

In the ECU 5, a plurality of programs related to the air-fuel ratio feedback control for engine and the like are being executed by the CPU 6. The abnormality diagnosing program included in these plurality of programs applies arithmetic processing to the obtained output (detection signal) of the wideband air-fuel ratio sensor 1, and thus diagnoses or determines whether the wideband air-fuel ratio sensor 1 is in abnormal state or not. Now, each process (operation) of the abnormality diagnosing program is explained based on flowcharts of FIGS. 4-7, with reference to FIGS. 1-3, 8 and 9. FIG. 4 is the flowchart showing a main routine of the abnormality diagnosing program. FIGS. 5-7 are the flowcharts showing the response-delay diagnosis processing which is called by the main routine of the abnormality diagnosing program. FIG. 8 is a timing chart showing one example of the appearance that the air-fuel ratio measured value varies by following the reversals (changes between rich and lean sides) of the target air-fuel ratio in the case that the gas sensor is not in abnormal state. FIG. 9 is a timing chart showing one example of the appearance that the air-fuel ratio measured value varies with delay by failing to follow the reversals (changes between rich and lean sides) of the target air-fuel ratio in the case that the gas sensor is in abnormal state. Hereinafter, each step of the respective flowcharts is abbreviated as "S", and each timing on time-axes (lateral axes) of the graphs shown in FIGS. 8 and 9 is abbreviated as "T".

The abnormality diagnosing program has been stored in the program storage area 71 of the ROM 7 shown in FIG. 2; and is executed by the CPU 6 together with the other programs for controlling the engine, when the ECU 5 is activated or powered.

When the main routine of the abnormality diagnosing program is started as shown in FIG. 4; at first, an initialization process is carried out to secure the storage areas for variables (parameters), flags, counters, and the like in the RAM 8 which are used by the abnormality diagnosing program. Then, the initialization condition flag of flag storage area 81 is set at 1 to enable the execution of abnormality diagnosis of the wideband air-fuel ratio sensor 1 (S10). Next, the sensor drive circuit section 3 of sensor unit 4 receives a command from the ECU 5, and thereby the heater voltage supply circuit 31 applies power to the heater member 27 in order to activate or energize the solid electrolyte layers 11, 13 and 14 of the wideband air-fuel ratio sensor 1 (see FIG. 1). The controller (ECU 5 or CPU 6) receives a sensor resistance-value signal indicative of an internal resistance value of the solid electrolyte layer 13, through an analog-digital conversion circuit (not shown) from the sensor unit 4. Then, the controller judges whether or not the wideband air-fuel ratio sensor 1 has been already activated by comparing a magnitude of this sensor resistance-value signal with the predetermined sensor-activation judging value stored in the set-value storage area 72 (S11). At this time, if it is determined that the wideband air-fuel ratio sensor 1 has not yet become activated (S11: NO), the controller repeatedly obtains the sensor resistance-value signal and compares this sensor resistance-value signal with the sensor-activation judging value until the wideband air-fuel ratio sensor 1 becomes activated.

Although not shown in FIG. 1, the sensor drive circuit section 3 is equipped with a sensor resistance-value sensing circuit known in the art. Specifically, this sensor resistance-value sensing circuit is adapted to sense a potential difference generated between electrodes 21 and 22 of the Vs cell as the sensor resistance-value signal, when a current supply circuit provided separately from the minute current supply circuit 34 periodically supplies a constant electric-current to the Vs cell. Then, the sensor resistance-value sensing circuit outputs this sensor resistance-value signal to the ECU 5. At this time, the temperature of the sensor element 10 can be detected based on the sensor resistance-value signal since there is a correlation between the temperature and the sensor resistance-value signal in the Vs cell of the sensor element 10.

As shown in FIG. 4, if it is determined that the wideband air-fuel ratio sensor 1 has become activated (S11: YES), a timer program (not shown) installed separately from the abnormality diagnosing program is called and started (S12). The timer program is a program configured to increment a counter value serving as the reference of a timing for executing respective processes of the abnormality diagnosing program, at certain time intervals. Alternatively, the timer program may be a program configured to decrement the counter value at the certain time intervals. The abnormality diagnosing program is configured to repeatedly execute the processes between S14 and S26 of the main routine, for example, once every 25 msec (milliseconds). The counter value is used for judging whether or not 25 msec have elapsed from a time point when the execution of the processes between S13 and S25 was started. Therefore, at the step S14, the current counter value of the timer program is reset, and a process for restarting the time measurement is carried out by regarding a current time point as a start point of the time measurement.

Next, the initialization condition flag of the flag storage area 81 is checked or referred to (S15). The initialization condition flag has been set at 1 at step S10, and hence the program proceeds to step S16 (S15: YES). At step S16, a process for resetting some of the flags which are used temporally in the abnormality diagnosing program is carried out. Specifically, the abnormality determination flag, the measurement completion flag, the initialization condition flag in the flag storage area 81 are respectively set or stored at 0. Subsequently at step S19, some of the flags which are used temporally in the abnormality diagnosing program, specifically, the target air-fuel ratio flag, the first-actual-air-fuel-ratio-moderated-value increase experience flag and the first-actual-air-fuel-ratio-moderated-value decrease experience flag in the flag storage area 81 are respectively set at 0. Moreover, respective variables which are used temporally in the abnormality diagnosing program, specifically, the target air-fuel-ratio reversal number of the target air-fuel-ratio reversal number storage area 87, the area total value of the area total value storage area 88 and the non-reversal number of the non-reversal number storage area 89 are also respectively set at 0. Then, the program proceeds to step S26.

At step S26, the counter value of the timer program started at step S12 is checked or referred to (by the controller based on the abnormality diagnosing program). The counter value has been reset at step S14. If the counter value is lower than a value corresponding to 25 msec at the time of check of step S26 (S26: NO), the controller waits ready and continues to refer to the counter value. If the counter value has become greater than or equal to the value corresponding to 25 msec (S26: YES); the program returns to step S14, and the counter value is reset again to repeat the processes between S15 and S26.

At step S15 on the second time around of routine, the initialization condition flag is at 0 (S15: NO). Accordingly, the program proceeds to step S18. At step S18, the operating-parameter condition flag of the flag storage area 81 is checked or referred to. As mentioned above, the value of the operating-parameter condition flag is managed by a control program(s) different from the abnormality diagnosing program. While the engine rotational speed and/or the cooling water temperature has not yet reached the predetermined value-range regarded as its normal level, the operating-parameter condition flag is maintained at its initial state, i.e., at 0 (S18: NO). Hence, the program proceeds to step S19. After resetting the above-mentioned respective flags and variables, the program proceeds to step S26. Then, the program waits for the lapse of 25 msec and returns to step S14 similarly as mentioned above.

If the engine rotational speed and/or the cooling water temperature has fallen within the predetermined value-range regarded as its normal level, and also has been maintained within this normal range for a predetermined time period; it is determined that operating-parameter conditions (criteria) have been satisfied. Hence, the above control program(s) different from the abnormality diagnosing program sets or stores the operating-parameter condition flag of the flag storage area 81 at 1. Thus at step S18, the abnormality diagnosing program can proceed to step S20 (S18: YES). Next at step S20, the measurement completion flag of the flag storage area 81 is checked or referred to. Since the measurement completion flag has been set at 0 by the process of step S16, the program proceeds to step S22 (S20: NO).

At step S22, the target air-fuel ratio is obtained (by the controller based on the abnormality diagnosing program). The ECU 5 is performing the so-called air-fuel ratio feedback control. In this air-fuel ratio feedback control, the air-fuel ratio of air-fuel mixture to be supplied to the engine is adjusted based on the information of the air-fuel ratio of exhaust gas obtained as the output of the wideband air-fuel ratio sensor 1, and the injection quantity and injection timing of fuel and the like are controlled in conformity with the adjusted value of air-fuel ratio of air-fuel mixture. Namely, such program for performing this air-fuel ratio feedback control sets the target air-fuel ratio which is a target for the air-fuel ratio of air-fuel mixture to be supplied to the engine, and controls the fuel injection according to this target air-fuel ratio, in order to adjust the air-fuel ratio of air-fuel mixture. At step S22, the target air-fuel ratio which has been set by such program and which is the newest value at the current timing (at execution timing of step S22) is obtained (by the controller based on the abnormality diagnosing program). Then, the obtained target air-fuel ratio is stored in the target air-fuel ratio storage area 82.

Next at step S23, the output (detection signal) of the wideband air-fuel ratio sensor 1, i.e., the air-fuel ratio measured value is obtained. The air-fuel ratio measured value is provided by converting the value of the pump current Ip passing through the Ip cell to its digital value as mentioned above. Then, the air-fuel ratio measured value is stored in the air-fuel-ratio measured value storage area 83. It is noted that this process of obtaining the detection signal derived from the wideband air-fuel ratio sensor 1 at constant time intervals (every 25 milliseconds in this embodiment) at step S23 corresponds to "detection signal obtaining step" according to the present invention, and the CPU 6 that executes this process corresponds to "detection signal obtaining section or means" according to the present invention.

At step S24, the response-delay diagnosis processing serving as a subroutine is called (see FIGS. 5-7). When the abnormality diagnosing program returns from the subroutine (from the response-delay diagnosis processing), the program proceeds to step S26. Then, the program returns to step S14 after holding on for the lapse of 25 msec. The measurement completion flag is maintained at 0 until the abnormality diagnosis for the wideband air-fuel ratio sensor 1 is completed. Therefore, the processes between step S14 and step S26 of the main routine continue to be carried out in the similar process sequence as explained above, and thereby the response-delay diagnosis processing continues to be executed every 25 msec. Here, the response-delay diagnosis processing shown in FIGS. 5-7 which is called by step S24 of the main routine is now explained referring to the timing chart of FIG. 8.

As shown in FIGS. 5-7, in the subroutine as the response-delay diagnosis processing, at first, the variation state of the target air-fuel ratio is checked by executing the processes between step S30 and step S34, and then a series of processes is selected according to the checked variation state. Specifically, the processes between step S42 and step S76 are executed only at the timings when the target air-fuel ratio moves (make a transition) from the rich side to the lean side. At the other timings, the processes between step S35 and step S39 are executed. After any one of these two series of processes (the processes between step S42 and step S76 or the processes between S35 and step S39) has been executed; common processes between step S80 and step S86 shown in FIG. 7 are executed, and the program returns to the main routine.

At first, the processes from step S30 to step S34 are now explained. As shown in FIG. 5, when the response-delay diagnosis processing is started, the target air-fuel ratio flag of the flag storage area 81 is checked or referred to at step S30. In an initial state (for example, at a timing T0 of FIG. 8), it has not yet been determined whether the target air-fuel ratio is rich or lean relative to the target center air-fuel ratio, and the target air-fuel ratio flag has been set at 0 by the process of step S19 (see FIG. 4). Namely in the initial state, the target air-fuel ratio flag provisionally indicates the state where the target air-fuel ratio is lean (S30: NO). At step S31, the target air-fuel ratio stored in the target air-fuel ratio storage area 82 is compared with the target center air-fuel ratio stored in the set-value storage area 72 in order to confirm whether an actual target air-fuel ratio is rich or lean, i.e., in the rich side or in the lean side. If the target air-fuel ratio is in the rich side; the target air-fuel ratio has a value lower than the target center air-fuel ratio (S31: YES), and thereby the target air-fuel ratio flag of the flag storage area 81 is set at 1 at step S32. Then, the program proceeds to step S35. At a next time of routine and subsequent routines (for example, routines between T0 and T1 in FIG. 8); the target air-fuel ratio flag has been set at 1 (S30: YES), and hence the program proceeds to step S33. While the target air-fuel ratio remains in the rich side, the target air-fuel ratio has a value lower than the target center air-fuel ratio (S33: NO), so that the program proceeds to step S35.

At a timing when the target air-fuel ratio enters (makes a transition) from the rich side into the lean side (for example, T1 of FIG. 8), the target air-fuel ratio becomes greater than or equal to the target center air-fuel ratio (S33: YES). Hence, the program proceeds to step S34. Then, the processes between step S42 and step S76 are carried out. Since the target air-fuel ratio flag is set at 0 at step S34, at a next time of routine and subsequent routines (for example, routines between T1 and T2 of FIG. 8), the program again comes to proceed to step S35. As explained above, only at the timings when the target air-fuel ratio moves from the rich side to the lean side (T1, T3, T5, T7, T9 and T11 in FIG. 8), the processes between steps S42 and S76 are executed, so that the program returns through the processes between steps S80 and S86 to the main routine. At the other timings, the processes between steps S35 and S39 are executed, so that the program returns through the processes between steps S80 and S86 to the main routine.

Next, the processes from step S35 to step S39 are now explained. The processes of steps S35 and S36 shown in FIG. 5 are provided for calculating the two kinds of (current) actual air-fuel ratio moderated values, namely the first actual air-fuel ratio moderated value and the second actual air-fuel-ratio moderated value, by applying the moderation calculation to the air-fuel ratio measured value. In FIG. 8, the air-fuel ratio measured value is shown by a solid line, the first actual air-fuel ratio moderated value is shown by an alternate long and short dash line, and the second actual air-fuel-ratio moderated value is shown by an alternate long and two short dashes line.

At first, the (previous) first actual air-fuel ratio moderated value (which has been set in its initial state at 0 by the initialization process of S10) stored in the actual air-fuel-ratio moderated value storage area 84 is updated to be overwritten with the (current) first actual air-fuel ratio moderated value. At step S35, the first actual air-fuel ratio moderated value is calculated based on the above-described formula ① by reading or loading the value of the moderation coefficient α stored in the set-value storage area 72, the previous (last-time) first actual air-fuel ratio moderated value, and the air-fuel ratio measured value stored in the air-fuel-ratio measured value storage area 83. This calculation result is stored in the actual air-fuel-ratio moderated value storage area 84 as the (current) first actual air-fuel ratio moderated value. It is noted that this process of calculating the first actual air-fuel ratio moderated value at step S35 corresponds to "first moderated signal calculating step" according to the present invention, and the CPU 6 that executes this process corresponds to "first moderated signal calculating section or means" according to the present invention.

Similarly, the (previous) second actual air-fuel ratio moderated value (which has been set in its initial state at 0 by the initialization process of S10) stored in the actual air-fuel-ratio moderated value storage area 84 is updated to be overwritten with the (current) second actual air-fuel ratio moderated value. At step S36, the second actual air-fuel ratio moderated value is calculated based on the above-described formula ② by reading or loading the value of the moderation coefficient β stored in the set-value storage area 72, the previous (last-time) second actual air-fuel ratio moderated value, and the air-fuel ratio measured value stored in the air-fuel-ratio measured value storage area 83. This calculation result is stored in the actual air-fuel-ratio moderated value storage area 84 newly as the (current) second actual air-fuel ratio moderated value. It is noted that this process of calculating the second actual air-fuel ratio moderated value at step S36 corresponds to "second moderated signal calculating step" according to the present invention, and the CPU 6 that executes this process corresponds to "second moderated signal calculating section or means" according to the present invention.

The processes of steps S38 and S39 are provided for updating the maximum value of first actual air-fuel ratio moderated value and the minimum value of first actual air-fuel ratio moderated value. These maximum and minimum values are used when counting the non-reversal number which serves as a parameter for determining (selectively employing) the abnormality diagnosing reference value at an after-mentioned step S63. At step S38, by comparing the (previous) maximum value of first actual air-fuel ratio moderated value with the (current) first actual air-fuel ratio moderated value stored in the actual air-fuel-ratio moderated value storage area 84, the larger one of the (current) first actual air-fuel ratio moderated value and the (previous) maximum value of first actual air-fuel ratio moderated value is stored in the first-actual-air-fuel-ratio-moderated-value maximum value storage area 85 as the (current) maximum value of first actual air-fuel ratio moderated value. Similarly at step S39, by comparing the (previous) minimum value of first actual air-fuel ratio moderated value with the (current) first actual air-fuel ratio moderated value, the smaller one of these values is stored in the first-actual-air-fuel-ratio-moderated-value minimum value storage area 86 as the (current) minimum value of first actual air-fuel ratio moderated value. After the processes of steps S35-S39, the program proceeds to step S80 shown in FIG. 7.

Next, the processes from step S80 to step S86 are now explained. The processes of steps S80 and S81 are provided for calculating an area(s') dimension surrounded by a graph (the alternate long and short dash line) of the first actual air-fuel ratio moderated value and a graph (the alternate long and two-short dashes line) of the second actual air-fuel ratio moderated value shown in FIG. 8, as the area total value. At first, at step S80 shown in FIG. 7, the absolute value of a difference between the current (this-time) first actual air-fuel ratio moderated value and the current (this-time) second actual air-fuel ratio moderated value is calculated as the deviation, by reading or loading these two moderated values. This deviation can be represented by a difference in height between the first actual air-fuel ratio moderated value and the second actual air-fuel ratio moderated value in FIG. 8 which are obtained at the execution timing of step S80. Next as shown in FIG. 7, the area total value is read or loaded from the area total value storage area 88 (in the initial state, the area total value has been stored at 0 by the process of S19), and the deviation calculated at step S80 is added to the area total value. This calculation result of addition is stored in the area total value storage area 88 by means of overwriting, at step S81. By repeating the execution of response-delay diagnosis processing, the deviations of respective timings are integrated with each other as the area total value (the deviation total value), as shown by a graph (a dotted line) of the area total value in FIG. 8. It is noted that the process of calculating the difference between the first actual air-fuel ratio moderated value and the second actual air-fuel ratio moderated value as the deviation at step S80 corresponds to "deviation calculating step" according to the present invention, and the CPU 6 that executes this process corresponds to "deviation calculating section or means" according to the present invention. Moreover, it is noted that the process of calculating the area total value (the deviation total value) resulting from the summation of all the deviations which are obtained during the diagnosis period by repeating the process of step S81 for the diagnosis period corresponds to "deviation total value calculating step" according to the present invention, and the CPU 6 that executes this process corresponds to "deviation total value calculating section or means" according to the present invention.

The processes between step S82 and step S86 shown in FIG. 7 are executed for the after-mentioned processes of steps S43-S49 which serve to check the variation state of the first actual air-fuel ratio moderated value, namely, serve to check whether or not the first actual air-fuel ratio moderated value has been reversed during the unit diagnosis period. Specifically, in the case where the first actual air-fuel ratio moderated value has experienced the increasing state or the decreasing state (i.e., has become in the increasing state or in the decreasing state) during the unit diagnosis period, its corresponding flag, i.e., the first-actual-air-fuel-ratio-moderated-value increase experience flag or the first-actual-air-fuel-ratio-moderated-value decrease experience flag is set at 1.

At first, a difference value between the (current) first actual air-fuel ratio moderated value and the maximum value of first actual air-fuel ratio moderated value updated at step S38 is calculated at step S82. If this difference value is greater than or equal to the variation reference value (S82: YES); it is determined that the (current) first actual air-fuel ratio moderated value has decreased from the past-obtained value thereof, namely the first actual air-fuel ratio moderated value is regarded as having experienced the decreasing state. Hence, the first-actual-air-fuel-ratio-moderated-value decrease experience flag of the flag storage area 81 is set at 1 at step S83, and then the program returns to the main routine. On the other hand, the difference value produced by subtracting the (current) first actual air-fuel ratio moderated value from the maximum value of first actual air-fuel ratio moderated value is lower than the variation reference value (S82: NO); a difference value produced by subtracting the minimum value of first actual air-fuel ratio moderated value from the (current) first actual air-fuel ratio moderated value is calculated in the similar manner as above. If this difference value is greater than or equal to the variation reference value (S85: YES); it is determined that the (current) first actual air-fuel ratio moderated value has increased from the past-obtained value thereof, namely the first actual air-fuel ratio moderated value is regarded as having experienced the increasing state. Hence, the first-actual-air-fuel-ratio-moderated-value increase experience flag of the flag storage area 81 is set at 1 at step S86, and then the program returns to the main routine. In the other cases (i.e., S82: NO and S85: NO), the program just returns to the main routine.

Thus, at any timings except the timings when the target air-fuel ratio moves from the rich side to the lean side (except T1, T3, T5, T7, T9 and T11 in FIG. 8), the processes of steps S35-S39 and steps S80-S86 are repeatedly executed. The deviation between the first actual air-fuel ratio moderated value and the second actual air-fuel ratio moderated value which have been obtained by moderating the air-fuel ratio measured value by means of the moderation calculation using the different moderation coefficients α and β is calculated at every execution of the response-delay diagnosis processing. Accordingly, the deviations are gradually integrated with one another as the area total value, as shown in FIG. 8.

Next, the processes between step S42 and step S76 which are executed at the timings when the target air-fuel ratio moves (makes a transition) from the rich side to the lean side are now explained. At first at step S42, the air-fuel ratio measured value of the air-fuel-ratio measured value storage area 83 is read and copied onto the respective (current) first actual air-fuel ratio moderated value and (current) second actual air-fuel ratio moderated value of the actual air-fuel-ratio moderated value storage area 84. In this embodiment, a process for bringing the moderated state (moderated degree) of each actual air-fuel ratio moderated value back to its initial state, i.e., back to not-moderated state is conducted substantially periodically at the timings when the target air-fuel ratio moves (enters) from the rich side to the lean side. Namely, in the calculation of the (current) first actual air-fuel ratio moderated value and (current) second actual air-fuel ratio moderated value which result from the moderation of the air-fuel ratio measured value with the use of the previously-calculated first and second actual air-fuel ratio moderated values, the (current) first actual air-fuel ratio moderated value and (current) second actual air-fuel ratio moderated value are reset at the occasions when the target air-fuel ratio reverses from the rich side to the lean side.

In the processes between steps S43 and S49, the non-reversal number of times is counted which is used as the parameter for determining (selectively employing) the abnormality diagnosing reference value. In these processes between steps S43 and S49, at the timings when the target air-fuel ratio moves from the rich side to the lean side, it is judged whether or not the first actual air-fuel ratio moderated value has been reversed during the (this-time around) unit diagnosis period. If there has been no reversal of the first actual air-fuel ratio moderated value during the unit diagnosis period, the non-reversal number of times is incremented. Specifically, in the case where the status of first-actual-air-fuel-ratio-moderated-value increase experience flag in the flag storage area 81 is "1" (S43: NO), and the status of first-actual-air-fuel-ratio-moderated-value decrease experience flag is also "1" (S44: NO); the program proceeds to step S48. That is, in this case, it is determined that the first actual air-fuel ratio moderated value has moved (has been reversed) from the increasing state into the decreasing state, or from the decreasing state into the increasing state during the unit diagnosis period. Thereby, the increment of the non-reversal number of times is not carried out.

On the other hand, in the case where at least any one of the statuses of first-actual-air-fuel-ratio-moderated-value increase experience flag and first-actual-air-fuel-ratio-moderated-value decrease experience flag is "0" (S43: YES, or S43: NO and S44: YES), the program proceeds to step S46. At step S46, a difference between the maximum value of first actual air-fuel ratio moderated value and the minimum value of first actual air-fuel ratio moderated value is calculated. If this difference is greater than a value equal to 0.02 (S46: YES), it is determined that a variation (moving) of first actual air-fuel ratio moderated value has certainly occurred during the unit diagnosis period. However, since this variation (moving) is in either one of the increasing state or the decreasing state, it is determined that the reversal of first actual air-fuel ratio moderated value has been absent. Thereby, the non-reversal number is incremented by one at step S47. Then, the program proceeds to step S48. It is noted that this process of incrementing the non-reversal number (of times) by 1 at step S47 corresponds to "non-transition number counting step" according to the present invention, and the CPU 6 that executes this process corresponds to "non-transition number counting section or means" according to the present invention.

If the difference between the maximum value of first actual air-fuel ratio moderated value and the minimum value of first actual air-fuel ratio moderated value is smaller than or equal to 0.02 (S46: NO); it is determined that the first actual air-fuel ratio moderated value has not varied, and has been a constant value. Thereby, the program proceeds to step S48. The difference between the maximum value of first actual air-fuel ratio moderated value and the minimum value of first actual air-fuel ratio moderated value becomes equal to 0 in the case where the air-fuel ratio measured value has not varied at all. Therefore, by not updating the non-reversal number in such case, a smaller value is selected as the abnormality diagnosing reference value so that an accuracy of after-explained judgment of the abnormal state can be enhanced.

At subsequent step S48, the statuses (values) of first-actual-air-fuel-ratio-moderated-value increase experience flag and first-actual-air-fuel-ratio-moderated-value decrease experience flag are reset at 0. At step S49, the maximum value of first actual air-fuel ratio moderated value and the minimum value of first actual air-fuel ratio moderated value are reset by copying the (current) first actual air-fuel ratio moderated value onto the respective maximum and minimum values. Thus, the respective flags and parameters for updating the non-reversal number are reset at the timings T1, T3, T5, T7, T9 and T11 (when this-time unit diagnosis period has just ended and next unit diagnosis period is started) when the target air-fuel ratio moves from the rich side to the lean side as shown in FIG. 8. Then, the program proceeds to step S55 shown in FIG. 6.

The processes between steps S55 and S61 shown in FIG. 6 are provided for judging a start timing and an end timing of the diagnosis period. As mentioned above, the diagnosis period is started when the target air-fuel ratio has just reversed from the rich side into the lean side, and then is ended when the number of times that the target air-fuel ratio has reversed from the rich side to the lean side reaches the reference reversal number. Accordingly, when the target air-fuel-ratio reversal number is smaller than the reference reversal number (S55: NO); the processes of steps S56-S58 are executed, and then the target air-fuel-ratio reversal number is incremented by one (i.e., added to 1) at step S61 every time the target air-fuel ratio reverses from in the rich side to in the lean side. Only in the case where the target air-fuel-ratio reversal number is equal to 0 (S56: YES); the area total value is reset at step S57, the non-reversal number is reset at step S58, and the program proceeds to step S61. By virtue of these processes, for example even if the response-delay diagnosis processing is started at timing T0 shown in FIG. 8, the updated non-reversal number and the area total value summed for the time interval between T0 and T1 are reset. Thereby, the diagnosis period is started at timing T1 when the target air-fuel ratio reverses from the rich side into the lean side for the first time. Since the target air-fuel-ratio reversal number is incremented by one at step S61 (see FIG. 6), the area total value and the non-reversal number are not reset when the target air-fuel ratio reverses from the rich side to the lean side after the timing T1 (i.e., T3, T5, T7, T9 and T11), so that the area total value and the non-reversal number respectively continue to be added or incremented for the diagnosis period. The target air-fuel-ratio reversal number continues to be incremented (S56: NO, S61) for the diagnosis period (also at timing T1). Then, the program proceeds to steps S80-S86 shown in FIG. 7, and returns to the main routine. It is noted that this process of incrementing the target air-fuel-ratio reversal number by 1 at step S61 corresponds to "target air-fuel-ratio reversal number counting step" according to the present invention, and the CPU 6 that executes this process corresponds to "target air-fuel-ratio reversal number counting section or means" according to the present invention.

Thus, the target air-fuel-ratio reversal number is incremented by one (added to 1) at step S61 every time the target air-fuel ratio reverses from the rich side to the lean side. When the target air-fuel-ratio reversal number is greater than or equal to the reference reversal number (5 times) at the execution time of step S55 (S55: YES); it is determined that the diagnosis period has ended. Accordingly, the processes of steps S63-S76 are executed, namely, the processes of diagnosing (determining) whether the wideband air-fuel ratio sensor 1 is in abnormal state or not are carried out.

At first, with reference to abnormality diagnosing reference-value-table storage area 73 of ROM 7, the abnormality diagnosing reference value is selected according to the non-reversal number (of times) counted during the diagnosis period as mentioned above. This selected abnormality diagnosing reference value is temporarily stored in a predetermined storage area of RAM 8 at step S63. Moreover, since it is determined that the diagnosis period has ended, the measurement completion flag of the flag storage area 81 is stored at 1 at step S71. Then, the area total value which has been obtained by integrating each deviation between the first actual air-fuel-ratio moderated value and the second actual air-fuel-ratio moderated value calculated during the diagnosis period is compared with the selected abnormality diagnosing reference value at step S73. At this time, if the area total value is greater than or equal to the abnormality diagnosing reference value (S73: NO), it is determined or diagnosed that a responsivity of output of the wideband air-fuel ratio sensor 1 is normal (proper), i.e., has no abnormality at step S76. Then, the program returns through the processes between steps S80 and S86 to the main routine. On the other hand, if the area total value is smaller than the abnormality diagnosing reference value (S73: YES), it is determined or diagnosed that the responsivity of output of the wideband air-fuel ratio sensor 1 is abnormal (improper), i.e., has some abnormality at step S75. At this step S75, the abnormality determination flag of the flag storage area 81 is stored at 1. Then, the program returns through the processes between steps S80 and S86 to the main routine. It is noted that the process of selecting the abnormality diagnosing reference value in accordance with the non-reversal number at step S63 corresponds to "threshold-value employing step" according to the present invention, and the CPU 6 that executes this process corresponds to "threshold-value employing section or means" according to the present invention. It is noted that the process of diagnosing (determining) whether or not the gas sensor is in the abnormal state by comparing the area total value with the abnormality diagnosing reference value at step S73 corresponds to "abnormality diagnosing step" according to the present invention, and the CPU 6 that executes this process corresponds to "abnormality diagnosing section or means" according to the present invention.

As shown in FIG. 8, in the case where the wideband air-fuel ratio sensor 1 is in the normal state and thereby the air-fuel ratio measured value is varying by suitably following the reversals of the target air-fuel ratio; the first actual air-fuel ratio moderated value also follows the reversals of the target air-fuel ratio, and experiences both of the increasing state and decreasing state (i.e., becomes in the increasing state and also in the decreasing state) during each unit diagnosis period. Accordingly, the non-reversal number of the first actual air-fuel ratio moderated value is equal to 0 at the end time of each diagnosis period, so that a relatively small value (for example, 5) is selected as the abnormality diagnosing reference value.

On the other hand, as shown in FIG. 9, in the case where the wideband air-fuel ratio sensor 1 is in the abnormal state and thereby the air-fuel ratio measured value is being delayed by failing to suitably follow the reversals of the target air-fuel ratio; the air-fuel ratio measured value varies slowly (gently) relative to the variation of the target air-fuel ratio, and therefore the area total value calculated for the diagnosis period becomes a relatively small value. In the unit diagnosis periods T1-T3, T5-T7 and T9-T11 respectively having time points T2a, T6a and T9a at which the first actual air-fuel ratio moderated value has reversed (has changed its direction between increasing direction and decreasing direction), the non-reversal number is not incremented. However, in the unit diagnosis periods T3-T5 and T7-T9 during which the first actual air-fuel ratio moderated value has not reversed, the non-reversal number is incremented. Thereby, the non-reversal number of first actual air-fuel ratio moderated value becomes equal to 2 at the end time of the diagnosis period. Accordingly, a greater value (for example, 8) than the above-mentioned case of FIG. 8 is selected as the abnormality diagnosing reference value. If it is judged that the wideband air-fuel ratio sensor 1 is in the abnormal state, the value (status) of the abnormality determination flag is set at 1. This value of abnormality determination flag is repeatedly referred to by the other program(s) executed by the CPU 6, and for example, the other program(s) informs the driver of the abnormal state if the abnormality determination flag is at 1 when referring to the abnormality determination flag.

In the processes between steps S14 and S26 on or after the next-time around of the main routine shown in FIG. 4, the program proceeds to step S26 since the measurement completion flag has been stored at 1 (S20: YES). Accordingly, the response-delay diagnosis processing is not executed.

It will be obvious that various kinds of modifications and variations of the above embodiment can be made according to the present invention. For example, although the response-delay diagnosis processing is carried out repeatedly every 25 milliseconds in the above embodiment, this process time-interval is not necessarily limited to 25 msec and can be set at any time-interval. Moreover, as mentioned above, the sensor drive circuit section 3 may be provided in the ECU 5 as one circuit section of the ECU 5. Alternatively, the sensor drive circuit section 3 may include a microcomputer capable of executing the abnormality diagnosing program.

Moreover, although the reference reversal number is five times in the above embodiment, the reference reversal number is not limited to this and may be once, twice, or equal to or more than six times. Similarly, the values of moderation coefficients $\alpha$ and $\beta$ used for the calculation of the air-fuel-ratio moderated values are not limited to 0.9 and 0.2, and may be preset at any values greater than 0 and lower than 1.

Moreover, the (current) second actual air-fuel-ratio moderated value may be calculated by further applying a moderation calculation to the (current) first actual air-fuel-ratio moderated value calculated from the air-fuel ratio measured value.

Figure 10:
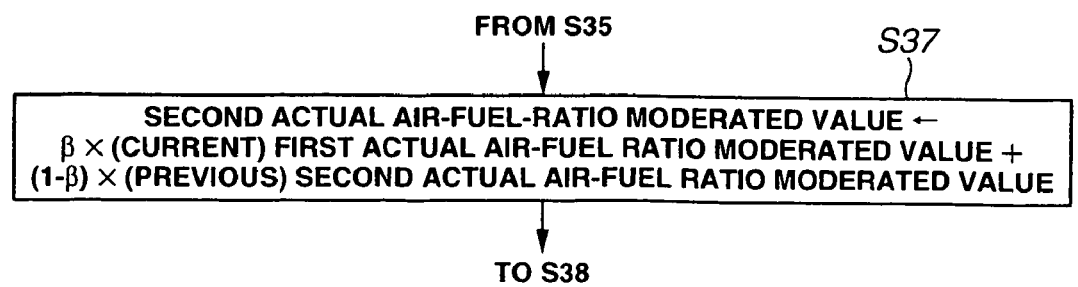
FIG. 10 is a flowchart showing a modified example of the response-delay diagnosis processing which is called by the main routine of the abnormality diagnosing program.

For example, a process of step S37 shown in FIG. 10 may be executed in place of the process of step S36 of FIG. 5. That is, the (current) second actual air-fuel ratio moderated value may be calculated by applying the moderation calculation given by the following formula (3).

Second actual air-fuel ratio moderated value=β×(current) first actual air-fuel ratio moderated value+ (1−β)×(previous) second actual air-fuel ratio moderated value     (3)

where, 0<β<1, for example, β=0.2 in this example

Thus, the diagnosis on presence or absence of abnormal state in the wideband air-fuel ratio sensor 1 may be carried out in accordance with a deviation between the first actual air-fuel-ratio moderated value and the second actual air-fuel-ratio moderated value calculated by the further moderation calculation using the first actual air-fuel-ratio moderated value. In such a case, the abnormality diagnosing reference value determined (selectively employed) based on the non-reversal number may be properly adjusted. Moreover in such a case where the second actual air-fuel-ratio moderated value is calculated based on the first actual air-fuel-ratio moderated value, the moderation coefficient β may be different from the moderation coefficient α or may be identical with the moderation coefficient α.

Moreover, although the area total value is calculated as a total value resulting from the addition of the deviations in the above embodiment, a value resulting from a multiplication of the deviations or a value resulting from an average of the deviations may be used as the area total value. In the case where such a value is used as the area total value, each abnormality diagnosing reference value can be set at an optimum threshold value according to the non-reversal number, which is produced through experiments or the like by calculating a value range obtainable under the normal state of the gas sensor and a value range obtainable under various abnormal states of the gas sensor. Although the abnormality diagnosing program is configured to become in a standby state after the first-time (entire) execution of the response-delay diagnosis processing for gas sensor, an execution number of times of the response-delay diagnosis processing is not limited to this. For example, the response-delay diagnosis processing may be carried out repeatedly between a time when the ignition key is turned on and a time when the ignition key is turned off.

Moreover, although the abnormality diagnosing reference value is determined or selected based on the non-reversal number (of times) of first actual air-fuel ratio moderated value in the above embodiment, the abnormality diagnosing reference value may be determined or selected based on a non-reversal number of the air-fuel ratio measured value or the second actual air-fuel-ratio moderated value by counting this non-reversal number. Alternatively, the abnormality diagnosing reference value may be determined or selected based on a number of times that the first actual air-fuel-ratio moderated value has reversed by following the reversals of the target air-fuel ratio.

Figure 11:
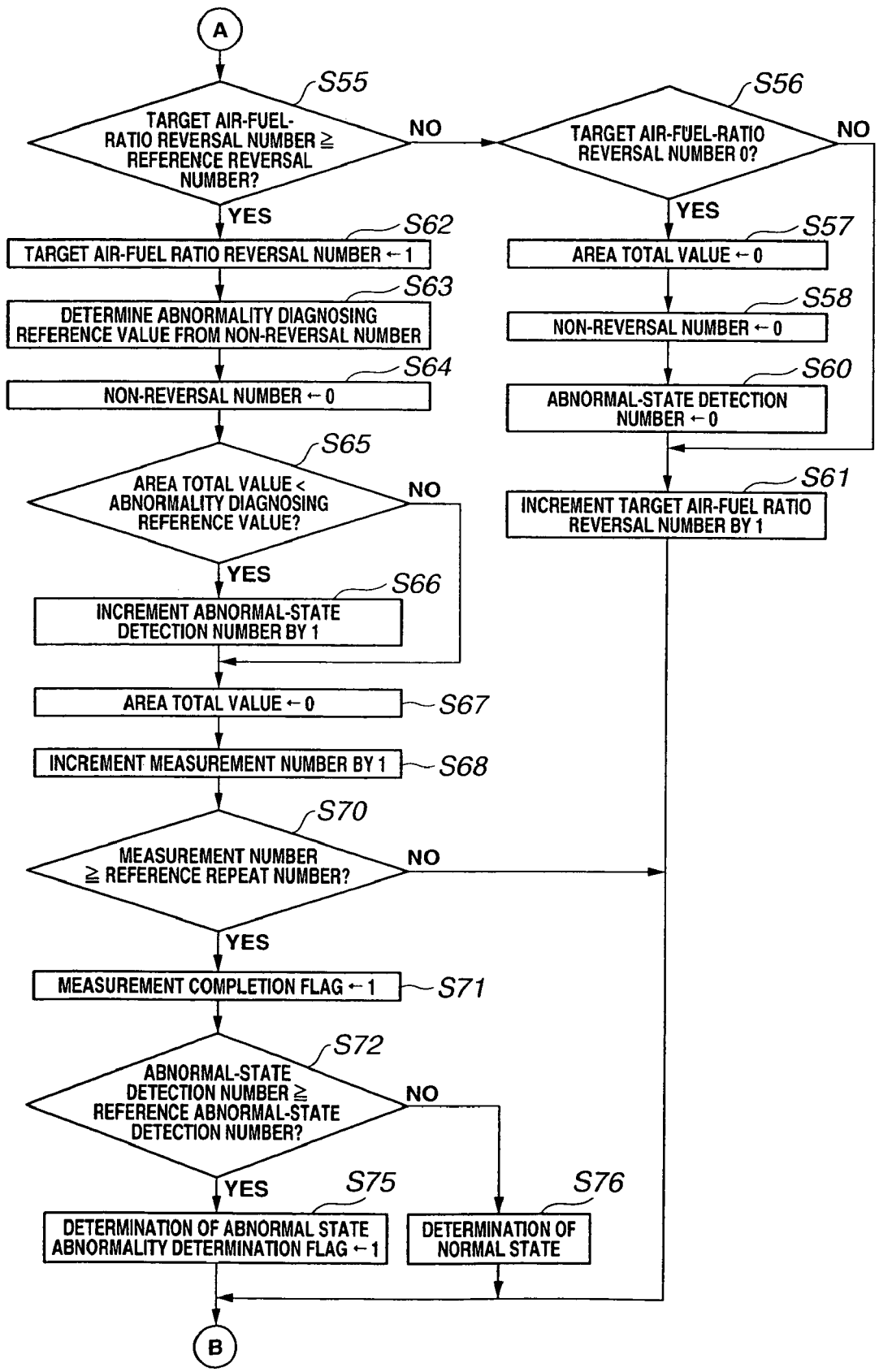
FIG. 11 is a flowchart showing the modified example of the response-delay diagnosis processing which is called by the main routine of the abnormality diagnosing program.

Moreover, by repeating the diagnosis period so as to have a plurality of diagnosis periods, a provisional judgment (preliminary diagnosis) about presence or absence of abnormal state in the gas sensor may be carried out every diagnosis period. Then, when the plurality of diagnosis periods have ended, a final judgment about presence or absence of abnormal state in the gas sensor may be made based on a number (of times) of the provisional judgments that the gas sensor is in the abnormal state. For example, a modified example of the processes between steps S55 and S76 of FIG. 6 included in the response-delay diagnosis processing of FIGS. 5-7 is shown in FIG. 11. In this modified embodiment, steps having the same processes as those of the above-described embodiment are given the same step numerals as those of the above-described embodiment.

In this modified embodiment, an abnormal-state detection number and a measurement number are newly provided as variables to be stored in predetermined storage areas (not shown) of the RAM 8. Moreover, a reference repeat number and a reference abnormal-state detection number have been stored in the set-value storage area 72 of the ROM 7. In this modified embodiment, it is judged whether or not the wideband air-fuel ratio sensor 1 is in the abnormal state every time each diagnosis period has ended. The abnormal-state detection number is a variable serving to count the number of times that it has been determined that the wideband air-fuel ratio sensor 1 is in the abnormal state. The abnormal-state detection number is stored at 0 as its initial value. Moreover, the measurement number is a variable serving to count the number of repetitions of the diagnosis period, and is stored at 0 as its initial value. The reference repeat number defines the number of times that the diagnosis period should be repeated (i.e., defines whole number of repetitions). In this modified embodiment, the reference repeat number has been stored at 3 (3 times). The reference abnormal-state detection number defines a threshold value (reference value) for making a finial decision on whether or not the wideband air-fuel ratio sensor 1 is in the abnormal state by comparing with the abnormal-state detection number when the plurality of diagnosis periods have just ended. In this modified embodiment, the reference abnormal-state detection number has been stored at 2 (2 times). In this modified embodiment, at step S19 of the main routine of abnormality diagnosing program in FIG. 4, the abnormal-state detection number and the measurement number are reset in addition to the resets of respective flags and variables described in the above (pre-modified) embodiment.

This modified embodiment is now explained with a central focus on the response-delay diagnosis processing and with the other parts abbreviated or simplified, since each process during individual diagnosis period is similar as that in the above embodiment.

Similarly as the above embodiment, the main routine of the abnormality diagnosing program is started by the CPU 6 as shown in FIG. 4. Then, when the certain condition (criterion) is satisfied by the case judgments (YES-NO judgments) using the initialization condition flag, the operating-parameter condition flag and the measurement completion flag; the response-delay diagnosis processing shown in FIGS. 5, 11 and 7 becomes capable of being carried out. Then, at the timing at which the target air-fuel ratio of air-fuel mixture has just reversed from in the rich side to in the lean side for the first time (S30: YES, S33: YES in FIG. 5, . . . , S55: NO, S56: YES in FIG. 11); the area total value and the non-reversal number are reset (S57, S58), the abnormal-state detection number is reset (S60), and the target air-fuel-ratio reversal number becomes equal to 1 by the process of step S61 so that a first diagnosis period is started. During the diagnosis period, similarly as the above (pre-modified) embodiment; the calculation of the first and second actual air-fuel-ratio moderated values at steps S35 and S36 in FIG. 5, the update of the maximum and minimum values of first actual air-fuel ratio moderated value at steps S38 and S39, the calculation of the deviation between the first and second actual air-fuel-ratio moderated values at step S80 in FIG. 7, the integration (summation) of the area total value at step S81, and the detection of the increasing and decreasing states of the first actual air-fuel ratio moderated value at steps S82-S86, are repeatedly carried out. When the target air-fuel ratio reverses from the rich side to the lean side, the non-reversal number is incremented at step S47 in FIG. 5 if the first actual air-fuel ratio moderated value has not been reversed during this-time unit diagnosis period (unit diagnosis period continued up to now). Then, the target air-fuel-ratio reversal number is incremented at step S61 in FIG. 11, and next unit diagnosis period is started. For the time interval produced by repeating the unit diagnosis periods, the area total value continues to be integrated or added. Then, when the target air-fuel-ratio reversal number becomes greater than or equal to the reference reversal number, for example, 5 times (S55: YES in FIG. 11); the first diagnosis period is ended.

Then, in order to start a second diagnosis period, the target air-fuel-ratio reversal number is set or stored at 1 at step S62 in FIG. 11. Next, the abnormality diagnosing reference value is selected according to the non-reversal number counted during the first diagnosis period, with reference to the abnormality diagnosing reference-value-table storage area 73. This abnormality diagnosing reference value is temporarily stored in the predetermined storage area of the RAM 8 at step S63. Moreover, the non-reversal number is reset at step S64 in order to count a new number of times of non-reversal during the second diagnosis period.

Next, the area total value obtained by integrating the deviations between the first actual air-fuel ratio moderated values and second actual air-fuel ratio moderated values respectively calculated during the first diagnosis period is compared with the above-mentioned selected abnormality diagnosing reference value at step S65. At this time, if the area total value takes a value greater than or equal to the abnormality diagnosing reference value (S65: NO), it is determined that the responsivity of output of the wideband air-fuel ratio sensor 1 has not become abnormal during the first diagnosis period. Then, the program proceeds to step S67. On the other hand, if the area total value takes a value smaller than the abnormality diagnosing reference value (S65: YES), it is determined that the responsivity of output of the wideband air-fuel ratio sensor 1 has become abnormal during the first diagnosis period. Hence, the abnormal-state detection number is incremented by 1 at step S66, and the program proceeds to step S67. It is noted that the process of provisionally judging whether or not the gas sensor is in the abnormal state by comparing the area total value with the abnormality diagnosing reference value at step S65 corresponds to "abnormal-state provisionally judging step" according to the present invention, and the CPU 6 that executes this process corresponds to "abnormal-state provisionally judging section or means" according to the present invention.

At step S67, the area total value is reset in order to newly calculating (integrating) the area total value during the second diagnosis period. At step S68, the measurement number stored in the predetermined storage area of the RAM 8 is incremented by 1 (the measurement number takes a value equal to 0 in its initial state). Next, at step S70, it is confirmed whether or not the measurement number becomes greater than or equal to the reference repeat number. In this process, it is confirmed whether or not the diagnosis period has been already repeated the number of times (e.g., 3 times) given by the reference repeat number. Since this criterion has not yet satisfied at the end time of the first diagnosis period (S70: NO), the program returns through steps S80-S86 shown in FIG. 7 back to the main routine. It is noted that the process of repeating the diagnosis period by maintaining the measurement completion flag at 0 until the measurement number becomes greater than or equal to the reference repeat number at step S70 corresponds to "repeatedly calculating step" according to the present invention, and the CPU 6 that executes this process corresponds to "repeatedly calculating section or means" according to the present invention.

With reference to the graphs shown in FIGS. 8 and 9, at the timing T11 at which the diagnosis period is terminated; the target air-fuel-ratio reversal number is set at 1, and the area total value is reset. Thereby, the similar condition as the timing T1 is set so as to start the diagnosis period again from the beginning, so that the area total value is newly calculated. Thus, the diagnosis period is repeated until the measurement number reaches the reference repeat number. If it is diagnosed that the responsivity of output of the wideband air-fuel ratio sensor 1 has been abnormal i.e., has some abnormality by comparing the abnormality diagnosing reference value with the area total value obtained during each diagnosis period, the abnormal-state detection number is incremented by one (S65: YES, S66).

As shown in FIG. 11, when the measurement number becomes greater than or equal to the reference repeat number, for example, when a third diagnosis period ends (S70: YES); the measurement completion flag is stored at 1 so as not to allow the main routine to call the response-delay diagnosis processing on next-time round and later, at step S71. Then, the abnormal-state detection number during the three diagnosis periods is compared with the reference abnormal-state detection number (e.g., 2 times) of the set-value storage area 72 at step S72. If the abnormal-state detection number is smaller than the reference abnormal-state detection number (S72: NO), it is finally diagnosed or determined that the responsivity in output of the wideband air-fuel ratio sensor 1 is normal (proper), i.e., has no abnormality at step S76. On the other hand, if the abnormal-state detection number is greater than or equal to the reference abnormal-state detection number (S72: YES); it is finally diagnosed that the output of the wideband air-fuel ratio sensor 1 is abnormal i.e., has some abnormality, and the abnormality determination flag of flag storage area 81 is stored at 1 at step S75. Then, this value (status) of the abnormality determination flag is used for the annunciation to the driver or the like. By so doing, even in the case where the wideband air-fuel ratio sensor 1 becomes transiently (only for a short while) in the abnormal state, it is not promptly determined that the wideband air-fuel ratio sensor 1 is abnormal. Therefore, the accuracy of abnormality diagnosis can be enhanced. It is noted that the process of making a final decision on whether or not the gas sensor is in the abnormal state by comparing the abnormal-state detection number with the reference abnormal-state detection number at step S72 corresponds to "abnormal-state finally judging step" according to the present invention, and the CPU 6 that executes this process corresponds to "abnormal-state finally judging section or means" according to the present invention.

Some advantages and effects according to the above-described embodiments (the pre-modified and modified embodiments) will be now briefly explained.

According to the above-described embodiments; the two moderated signals (first and second moderated signals) having moderation degrees different from each other are calculated by applying the plurality of moderation calculations to the detection signal outputted by the gas sensor, for the lapse of the diagnosis period. Moreover, the deviation (difference) between the first and second moderated signals is calculated, and then it is diagnosed whether or not the gas sensor is in the abnormal state from the calculated deviation. The first and second moderated signals are calculated based on the detection signal of the gas sensor, and vary so as to follow the variation of the detection signal at slow paces different from each other. Accordingly, even if the value of detection signal outputted from the gas sensor targeted for the abnormality diagnosis tends to indicate an upper-side value or a lower-side value than its aim value (ideal spec value) under the influence of the variations in individuals (manufacturing tolerance) of gas sensor and/or sensor drive circuit section thereof, the first and second moderated signals calculated based on this detection signal also vary so as to follow the variation of the detection signal of the targeted gas sensor. That is, since the deviation (difference) which is used as the reference for diagnosing whether or not the gas sensor is in the abnormal state is calculated from the first and second moderated signals respectively following the variation of detection signal of the gas sensor, the above-mentioned influence of the variations in individuals can be reduced. Therefore, it can be suppressed that the calculated deviations are dispersed, i.e., take different values among respective gas sensors due to the variations in individuals (manufacturing tolerance) even if the respective gas sensors are in the same deterioration degree as one another. Thus, in the abnormality diagnostic method and apparatus according to the above embodiments, the diagnosis on presence or absence of abnormal state in the gas sensor can be performed more accurately.

Moreover, according to the above-described embodiments, these first and second moderated signals are calculated by applying the respective moderation calculations using the moderation coefficients (first and second moderation coefficients) different from each other, to the detection signal. Moreover, the second moderated signal may be calculated by applying a moderation calculation using one of the first and second moderation coefficients, to the first moderated signal calculated by applying the moderation calculation using the first moderation coefficient to the detection signal. By virtue of the applying of such moderation calculations, the first and second moderated signals having moderation degrees different from each other can be easily obtained based on the detection signal of gas sensor.

Moreover, according to the above-described embodiments, the possible range of the deviation calculated from the first and second moderated signals in order to diagnose whether or not the gas sensor is in the abnormal state can be adjusted by suitably combining the first moderation coefficient and the second moderation coefficient. As the moderation degree of each of the first and second moderated signals is made to be smaller, a detection-signal follow-up capability of the first or second moderated signal can be more enhanced when the detection signal indicates an instantaneously great variation (i.e., moves sharply). On the other hand, as the moderation degree of the first or second moderated signal is made to be greater, the detection-signal follow-up capability can be adjusted lower. Accordingly, by suitably adjusting the combination of the first and second moderation coefficients, a sensibility for the abnormal-state diagnosis of gas sensor can be adjusted so that the accuracy of the abnormality diagnosis can be more improved.

Although the abnormality diagnosis for a gas sensor may be performed on the basis of an individual of the deviations calculated at constant time intervals at which the detection signals are obtained, the abnormality diagnosis for a gas sensor is performed by using the deviation total value which is a total of all the deviations obtained during the diagnosis period, according to the above-described embodiments. Therefore, the distinction between a range of deviation total value obtainable under the normal state of sensor and a range of deviation total value obtainable under the abnormal state of sensor can be made clearer so that the diagnosis on the abnormal state of gas sensor can be performed more accurately.

Moreover, according to the above-described modified embodiment; the abnormality diagnosis for gas sensor is carries out every diagnosis period by repeating the diagnosis period for the plurality of diagnosis periods, and then the number of times that it has been (provisionally) judged that the gas sensor is in the abnormal state is counted, so that the final decision is made on whether the gas sensor is in the abnormal state on the basis of this counted number. Accordingly, even in the case where the gas sensor indicates the abnormal state transiently (for a short while), it is not promptly determined that the gas sensor is abnormal. Therefore, the diagnosis on presence or absence of abnormal state in the gas sensor can be carried out more accurately.

When trying to perform an air-fuel ratio feedback control reversing the target air-fuel ratio of an air-fuel mixture to be supplied to an internal combustion engine from a rich side to a lean side or from the lean side to the rich side through a specific air-fuel ratio defined as the boundary of the rich and lean sides, generally, a feedback correction is performed to bring an air-fuel ratio (actual air-fuel ratio) calculated based on the detection signal of gas sensor closer to the target air-fuel ratio. In the case where the deterioration (response deterioration) of gas sensor has occurred in the internal combustion engine performing such an air-fuel ratio feedback control, the deviation between the first and second moderated signals becomes small as compared with its normal (not-deteriorated) state if its deterioration degree is light. On the other hand, if its deterioration degree is high (the deterioration of gas sensor has progressed excessively); the deviation between the first and second moderated signals contrary becomes relatively large, and thereby there is a possibility that the diagnosis on the abnormal state of gas sensor cannot be performed properly.

For example, when thinking about the case that the deterioration (response deterioration) of gas sensor has progressed to a state delaying the response of detection signal of gas sensor relative to the reversal of target air-fuel ratio by a half cycle (half period) of variation of the target air-fuel ratio, the detection signal of gas sensor indicates an output value corresponding to the lean side although the target air-fuel ratio is in the rich side. In such a situation, when the air-fuel ratio (actual air-fuel ratio) calculated based on the above detection signal is brought closer to the target air-fuel ratio by way of feedback correction, this feedback correction becomes excessive. Due to this, the detection signal of gas sensor indicates a value corresponding to richer side (than the case of no feedback) when the target air-fuel ratio moves in the lean side at the next time. Then, when such a situation is repeated, the detection signal of gas sensor is outputted under a more enlarged (excessively amplified) state. Thereby, there is a possibility that the deviation between the first and second moderated signals does not become small although the deterioration of gas sensor has progressed, so that the distinction from a normal (not-deteriorated) gas sensor cannot be properly achieved.

Therefore, according to the above-described embodiments, the threshold value for determining whether or not the gas sensor is in the abnormal state is changed according to a frequency with which the first moderated signal or the second moderated signal has made at least one of the transition (reversal) from increasing state to decreasing state and the transition from decreasing state to increasing state during the diagnosis period. Accordingly, the diagnosis on the abnormal state of gas sensor can be accurately performed even if the diagnosis period is started under the condition where the deteriorated state of gas sensor has excessively progressed. In other words, according to the above-described embodiments of the present invention, the abnormality diagnosis for gas sensor can be accurately achieved even if the diagnosis period for the abnormality diagnosis starts to be executed at any timing regardless of the progressing state of deterioration in the gas sensor.

Moreover, according to the above-described embodiments, the number of unit diagnosis periods during each of which the first moderated signal or second moderated signal has made neither the transition (reversal) from increasing state to decreasing state nor the transition from decreasing state to increasing state is calculated from all the unit diagnosis periods which are given by delimiting or dividing the diagnosis period every time the reversal number of times is incremented. Then, the threshold value predetermined according to the non-transition number counted during the diagnosis period is employed. Accordingly, it can be accurately diagnosed whether or not the gas sensor is in the abnormal state even if the obtainable range of the deviation total value is varied because the diagnosis period is started at any timing (any deteriorated state).

Moreover, according to the above-described embodiments, the above-mentioned abnormality diagnostic method and apparatus for gas sensor is applied to an oxygen sensor adapted to vary the output value of its detection signal substantially linearly with oxygen concentration in the exhaust gas. Accordingly, the abnormal state of this oxygen sensor can be detected accurately and reliably.

This application is based on prior Japanese Patent Application No. 2007-2578.07 filed on Oct. 1, 2007. The entire contents of this Japanese Patent Application are hereby incorporated by reference.

Although the invention has been described above with reference to certain embodiments of the invention, the invention is not limited to the embodiments described above. Modifications and variations of the embodiments described above will occur to those skilled in the art in light of the above teachings. The scope of the invention is defined with reference to the following claims.

What is claimed is:

1. A gas sensor diagnostic method for diagnosing whether a gas sensor is in an abnormal state or not on the basis of a detection signal outputted by the gas sensor exposed in an exhaust gas exhausted from an internal combustion engine, the detection signal representing a concentration of a specific gas component in the exhaust gas, the gas sensor diagnostic method comprising:
    a target air-fuel-ratio reversal number counting step of counting the reversal number of times that a target air-fuel ratio for an air-fuel mixture to be supplied to the internal combustion engine reverses from a rich side to a lean side or from the lean side to the rich side through a specific air-fuel ratio defined as a boundary of the rich and lean sides;
    a detection signal obtaining step of obtaining the detection signal of the gas sensor at constant time intervals during a diagnosis period which is a period between a timing when the reversal number of times starts to be counted and a timing when the reversal number of times reaches a predetermined number of times;
    a moderated signal calculating step of calculating
        a first moderated signal by applying a first moderation calculation to the obtained detection signal, and
        a second moderated signal by applying a second moderation calculation different from the first moderation calculation, to the obtained detection signal;
    a deviation calculating step of calculating a deviation between the calculated first moderated signal and second moderated signal; and
    an abnormality diagnosing step of determining whether the gas sensor is in the abnormal state or not on the basis of the deviation obtained during the diagnosis period.

2. The gas sensor diagnostic method as claimed in claim 1, wherein the moderated signal calculating step includes
    a first moderated signal calculating step of calculating the first moderated signal by applying the first moderation calculation using a predetermined first moderation coefficient to the obtained detection signal, and
    a second moderated signal calculating step of calculating the second moderated signal by applying the second moderation calculation using a second moderation coefficient to the obtained detection signal, the second moderation coefficient being predetermined to moderate the detection signal to a greater degree than the first moderation coefficient.

3. The gas sensor diagnostic method as claimed in claim 1, wherein the moderated signal calculating step includes
    a first moderated signal calculating step of calculating the first moderated signal by applying the first moderation calculation using a predetermined first moderation coefficient to the obtained detection signal, and
    a second moderated signal calculating step of calculating the second moderated signal by applying the second moderation calculation using one of the first moderation coefficient and a second moderation coefficient, to the first moderated signal,
    the second moderation coefficient being predetermined to take a different value from the first moderation coefficient.

4. The gas sensor diagnostic method as claimed in claim 1, further comprising
    a deviation total value calculating step of calculating a deviation total value resulting from a total of all the deviations obtained during the diagnosis period at the deviation calculating step,
    wherein the abnormality diagnosing step includes an operation of determining whether the gas sensor is in the abnormal state or not on the basis of a comparison result between the deviation total value and a predetermined threshold value.

5. The gas sensor diagnostic method as claimed in claim 1, further comprising
    a deviation total value calculating step of calculating a deviation total value resulting from a total of all the deviations obtained during the diagnosis period at the deviation calculating step; and
    a repeatedly calculating step of repeating the calculation of the deviation total value during the diagnosis period, for the plurality of diagnosis periods,
    wherein the abnormality diagnosing step includes
    an abnormal-state provisionally judging step of provisionally judging whether or not the gas sensor is in the abnormal state during each of the plurality of diagnosis periods, by comparing a predetermined threshold value with each of the calculated plurality of deviation total values, and
    an abnormal-state finally judging step of making a final decision on whether or not the gas sensor is in the abnormal state, on the basis of the number of times that it has been provisionally judged that the gas sensor is in the abnormal state at the abnormal-state provisionally judging step.

6. The gas sensor diagnostic method as claimed in claim 4, further comprising
a threshold-value changing step of changing the threshold value in accordance with a frequency with which the first moderated signal or the second moderated signal has made at least one of a transition from an increasing state to a decreasing state and a transition from the decreasing state to the increasing state during the diagnosis period.

7. The gas sensor diagnostic method as claimed in claim 6, wherein the threshold-value changing step includes
a non-transition number counting step of counting the number of unit diagnosis periods during each of which the first moderated signal or the second moderated signal has made neither the transition from the increasing state to the decreasing state nor the transition from the decreasing state to the increasing state, as a non-transition number, from all unit diagnosis periods which are given by delimiting the diagnosis period every time the reversal number of times is incremented during the diagnosis period, and
a threshold-value employing step of employing a value predetermined according to the counted non-transition number, as the threshold value.

8. The gas sensor diagnostic method as claimed in claim 1, wherein the gas sensor is an oxygen sensor adapted to vary an output value of its detection signal substantially linearly with an oxygen concentration in the exhaust gas.

9. A gas sensor diagnostic apparatus adapted to diagnose whether a gas sensor is in an abnormal state or not on the basis of a detection signal outputted by the gas sensor exposed in an exhaust gas exhausted from an internal combustion engine, the detection signal representing a concentration of a specific gas component in the exhaust gas, the gas sensor diagnostic apparatus comprising:
a target air-fuel-ratio reversal number counting section configured to count the reversal number of times that a target air-fuel ratio for an air-fuel mixture to be supplied to the internal combustion engine reverses from a rich side to a lean side or from the lean side to the rich side through a specific air-fuel ratio defined as a boundary of the rich and lean sides;
a detection signal obtaining section configured to obtain the detection signal of the gas sensor at constant time intervals during a diagnosis period which is a period between a timing when the reversal number of times starts to be counted and a timing when the reversal number of times reaches a predetermined number of times;
a moderated signal calculating section configured to calculate
a first moderated signal by applying a first moderation calculation to the obtained detection signal, and
a second moderated signal by applying a second moderation calculation different from the first moderation calculation, to the obtained detection signal;
a deviation calculating section configured to calculate a deviation between the calculated first moderated signal and second moderated signal; and
an abnormality diagnosing section configured to determine whether the gas sensor is in the abnormal state or not on the basis of the deviation obtained during the diagnosis period.

10. The gas sensor diagnostic apparatus as claimed in claim 9, wherein the moderated signal calculating section includes
a first moderated signal calculating section configured to calculate the first moderated signal by applying the first moderation calculation using a predetermined first moderation coefficient to the obtained detection signal, and
a second moderated signal calculating section configured to calculate the second moderated signal by applying the second moderation calculation using a second moderation coefficient to the obtained detection signal, the second moderation coefficient being predetermined to moderate the detection signal to a greater degree than the first moderation coefficient.

11. The gas sensor diagnostic apparatus as claimed in claim 9, wherein the moderated signal calculating section includes
a first moderated signal calculating section configured to calculate the first moderated signal by applying the first moderation calculation using a predetermined first moderation coefficient to the obtained detection signal, and
a second moderated signal calculating section configured to calculate the second moderated signal by applying the second moderation calculation using one of the first moderation coefficient and a second moderation coefficient, to the first moderated signal,
the second moderation coefficient being predetermined to take a different value from the first moderation coefficient.

12. The gas sensor diagnostic apparatus as claimed in claim 9, further comprising
a deviation total value calculating section configured to calculate a deviation total value resulting from a total of all the deviations obtained by the deviation calculating section during the diagnosis period,
wherein the abnormality diagnosing section is configured to determine whether the gas sensor is in the abnormal state or not on the basis of a comparison result between the deviation total value and a predetermined threshold value.

13. The gas sensor diagnostic apparatus as claimed in claim 9, further comprising
a deviation total value calculating section configured to calculate a deviation total value resulting from a total of all the deviations obtained by the deviation calculating section during the diagnosis period; and
a repeatedly calculating section configured to repeat the calculation of the deviation total value during the diagnosis period, for the plurality of diagnosis periods,
wherein the abnormality diagnosing section includes
an abnormal-state provisionally judging section configured to provisionally judge whether or not the gas sensor is in the abnormal state during each of the plurality of diagnosis periods, by comparing a predetermined threshold value with each of the calculated plurality of deviation total values, and
an abnormal-state finally judging section configured to make a final decision on whether or not the gas sensor is in the abnormal state, on the basis of the number of times that it has been provisionally judged that the gas sensor is in the abnormal state by the abnormal-state provisionally judging section.

14. The gas sensor diagnostic apparatus as claimed in claim 12, further comprising
a threshold-value changing section configured to change the threshold value in accordance with a frequency with which the first moderated signal or the second moderated signal has made at least one of a transition from an increasing state to a decreasing state and a transition from the decreasing state to the increasing state during the diagnosis period.

15. The gas sensor diagnostic apparatus as claimed in claim 14, wherein the threshold-value changing section includes a non-transition number counting section configured to count the number of unit diagnosis periods during each of which the first moderated signal or the second moderated signal has made neither the transition from the increasing state to the decreasing state nor the transition from the decreasing state to the increasing state, as a non-transition number, from all unit diagnosis periods which are given by delimiting the diagnosis period every time the reversal number of times is incremented during the diagnosis period, and a threshold-value employing section configured to employ a value predetermined according to the counted non-transition number, as the threshold value.

16. The gas sensor diagnostic apparatus as claimed in claim 9, wherein the gas sensor is an oxygen sensor adapted to vary an output value of its detection signal substantially linearly with an oxygen concentration in the exhaust gas.

* * * * *